US007226902B2

(12) United States Patent
Winkler et al.

(10) Patent No.: US 7,226,902 B2
(45) Date of Patent: Jun. 5, 2007

(54) LIGANDS FOR TGF-BETA BINDING PROTEINS AND USES THEREOF

(75) Inventors: David G. Winkler, Seattle, WA (US); John Latham, Seattle, WA (US); John Skonier, Shoreline, WA (US); Diana Shpektor, Bothell, WA (US); Trenton Hayes, Seattle, WA (US); James Geoghegan, Seattle, WA (US)

(73) Assignee: Celltech R&D, Inc., Bothell, WA (US)

( * ) Notice: Subject to any disclaimer, the term of this patent is extended or adjusted under 35 U.S.C. 154(b) by 153 days.

(21) Appl. No.: 10/799,162

(22) Filed: Mar. 12, 2004

(65) Prior Publication Data

US 2005/0085418 A1    Apr. 21, 2005

Related U.S. Application Data

(60) Provisional application No. 60/455,253, filed on Mar. 14, 2003.

(51) Int. Cl.
*C07K 14/00* (2006.01)
*A61K 38/00* (2006.01)

(52) U.S. Cl. .......................................... 514/2; 530/350
(58) Field of Classification Search ...................... None
See application file for complete search history.

(56) References Cited

U.S. PATENT DOCUMENTS

| 5,780,263 A | 7/1998 | Hastings et al. |
| 6,117,911 A * | 9/2000 | Grainger et al. ............ 514/648 |
| 6,395,511 B1 | 5/2002 | Brunkow et al. |
| 6,489,445 B1 | 12/2002 | Brunkow et al. |
| 6,495,738 B1 | 12/2002 | Brunkow et al. |

FOREIGN PATENT DOCUMENTS

| WO | WO-98/21335 | 5/1998 |
| WO | WO-99/03996 | 1/1999 |
| WO | WO-99/15556 | 4/1999 |
| WO | WO-01/64885 | 9/2001 |

OTHER PUBLICATIONS

Sivakumar et al., 2006, J cell Sci., 119(7):1350-1360.*
Balemans and Van Hul, Dev. Biol., 2002, 250:231-250.*
Balemans et al., *Extracellular Regulation of BMP Signaling in Vertebrates: A Cocktail of Modulators*, Developmental Biology 250:231-250, 2002.
Bondestam, *Ligands & Signaling Components of the Transforming Growth Factor β Family*, Helsinki University Biomedical Dissertations No. 17, 2002.
Ebara et al., *Mechanism for the Action of Bone Morphogenetic Proteins and Regulation of Their Activity*, Spine, 27(165):S10-S15, 2002.
Groppe et al., *Structural Basis of BMP Signalling Inhibition by the Cystine Knot Protein Noggin*, Nature, 420:636-642, 2002.
Koli et al., *Latency, Activation, and Binding Proteins of TGF-β*, Microscopy Research and Technique, 52:354-362, 2001.
Von Bubnoff et al., *Intracellular BMP Signaling Regulation in Vertebrates: Pathway or Network?*, Developmental Biology; 239:1-14, 2001.
Oelgeschlager et al., *The Evolutionarily Conserved BMP-Binding Protein Twisted Gastrulation Promotes BMP Signaling*, Nature 105:757-763, 2000.
Reddi, *Interplay Between Bone Morphogenetic Proteins and Cognate Binding Proteins in Bone Cartilage Development: Noggin, Chordin and DAN*, Arthritis Research, 3(1):1-5.
Khalil, *TGF-β: From Latent to Active*, Microbes and Infection, 1255-1263, 1999.
Lian et al., *Bone Formation: Osteoblast Lineage Cells, Growth Factors, Matrix Proteins, and the Mineralization Process*, Primer on the Metabolic Bone Diseases and Disorders of Mineral Metabolism, 4th Edition, 14-29, 1999.
Pittenger et al., *Multilineage Potential of Adult Human Mesenchymal Stem Cells*, Science, 284:143-147, 1999.
Schmitt et al., *Bone Morphogenetic Proteins: An Update on Basic Biology and Clinical Relevance*, Journal of Orthopaedic Research, 17:269-278, 1999.
Smith, *TGF β Inhibitors New and Unexpected Requirements in Vertebrate Development*, TIG, 15(1):3-5, 1999.
Hsu et al., *The Xenopus Dorsalizing Factor Gremlin Identifies a Novel Family of Secreted Proteins that Antagonize BMP Activities*, Molecular Cell, 1:673-683, 1998.
Iemura et al., *Direct Binding of Follistatin to a Complex of Bone-Morphogenetic Protein and its Receptor Inhibits Ventral and Epidermal Cell Fates in Early Xenopus Embryo*, Proc. Natl. Acad. Sci. USA, 95:9337-9342, 1998.
Durham et al., *Alterations in Insulin-Like Growth Factor (IGF)-Dependent IGF-Binding Protein-4 Proteolysis in Transformed Osteoblastic Cells*, Endocrinology, 136(4):1374-1380, 1995.
Miyazono et al., *Transforming Growth Factor-β: Latent Forms, Binding Proteins and Receptors*, Growth Factors, 8:11-22, 1993.
Pockwinse et al., *Expression of Cell Growth and Bone Specific Genes at Single Cell Resolution During Development of Bone Tissue-Like Organization in Primary Osteoblast Cultures*, Journal of Cellular Biochemistry, 49:310-323, 1992.

(Continued)

*Primary Examiner*—Eileen B. O'Hara
*Assistant Examiner*—Xiaozhen Xie
(74) *Attorney, Agent, or Firm*—Marshall, Gerstein & Borun LLP

(57) ABSTRACT

Compositions and methods are provided that relate to the unexpected specific association of (i) the TGF-beta binding protein sclerostin with the BMP antagonist protein chordin to form a complex, and of (ii) the TGF-beta binding protein sclerostin with the BMP antagonist protein noggin to form a complex, either of which complex is incapable of binding to a TGF-beta superfamily member such as a BMP. The invention provides isolated complexes for use in screening assays to identify agents that modulate bone mineralization, and offers other related advantages.

3 Claims, 9 Drawing Sheets

OTHER PUBLICATIONS

Riggs, *Overview of Osteoporosis*, The Western Journal of Medicine, 154:63-77, 1991.

Groppe et al., *Structural Basis of BMP Signalling Inhibition by the Cystine Knot Protein Noggin*, Nature, 420(6916):636-642, 2002.

Balemans et al., *Increased Bone Density in Sclerosteosis is Due to the Deficiency of a Novel Secreted Protein (SOST)*, Human Molecular Genetics, 10(5):537-543, 2001.

* cited by examiner

Common Cysteine Backbone

```
                    1                                                     50
    human-gremlin.pro  ----------  ----------  ----------  ----------  ----------
   human-cerberus.pro  MHLLLFQLLV  LLPLGKTTRH  QOGRQNQSSL  SPVLLPRNQR  ELPIGNHEEA
       human-dan.pro  ----------  ----------  ----------  ----------  ----------
      human-beer.pro  ----------  ----------  ----------  ----------  ----------

51                                                    100
    human-gremlin.pro  ----------  ------M     SRTAYTVGAL  LLLLGTLLPA  AEGKKKGSQG
   human-cerberus.pro  EEKPDLFVAV  PHLVAT.SPA  GEQQRQREKM  LSRFGRFWKK  PERDMHPSRD
       human-dan.pro  ----------  ----------  ----------  ----------  ----------
      human-beer.pro  ----------  ----------  ----------  -----MQLPLA  LCLVCLLVHT 101                                                    150
    human-gremlin.pro  AI.PPPDKAQ  HNDSEQTQSP  QQPGSRNRGR  GQGRGTAMPG  EEVLESSQEA
   human-cerberus.pro  SDSEPFPPGT  QSLIQPID.G  MKMEKSPLRE  EAKKFWHHFM  FRKTPASQGV
       human-dan.pro  ----------  ----------  ----------  MLRVLVGAVL  PAMLLAAPPP
      human-beer.pro  AFRVVEGQGW  QAFKNDATEI  IPELGEYPEP  PPELENNKTM  NRAENGGRPP 151          ↓           ↓           ↓           ↓    200
    human-gremlin.pro  LHVTERKYLK  RDWCKTQPLK  QTTIHEEGCNS  RTTINRF.CY  GQCNSFYIPR
   human-cerberus.pro  ILPIKSHEVH  WETCRTVPFS  QTTTHEGCEK  VVVQNNL.CF  GKCGSVHFP.
       human-dan.pro  INKLALFPDK  SAWCEAKNIT  QIVGHSGCEA  KSIQNRA.CL  GQCFSYSVPN
      human-beer.pro  HHPFETKDVS  EYSCRELHFT  RYVTDGPCRS  AKPVTELVCS  GQCGPARLLP 201           ↓           ↓                         250
    human-gremlin.pro  HIRKEEGSFQ  SCSF...CKP  KKFTTMHVTL  NCPELQPPTK  K.KRVTRVKQ
   human-cerberus.pro  ..GAAQHSHT  SCSH...CLP  AKFTTMHLPL  NCTELSSVIK  V...VMLVEE
       human-dan pro  TFPQSTESLV  HCDS...CMP  AQSMWEIVTL  ECPGHEEVPR  VDKLVEKILH
      human-beer.pro  NAIGRGKWWR  PSGPDFRCIP  DRYRAQRVQL  LCPGGEAPRA  RKVRLVAS..

↓51↓                                                  300
    human-gremlin.pro  CRC.ISIDLD  ----------  ----------  ----------  ----------
   human-cerberus.pro  CQCKVKTEHE  DGHILHAGSQ  DSFIPGVSA-  ----------  ----------
       human-dan.pro  CSCQACGKEP  SHEGLSVYVQ  GEDGPGSQPG  THPHPHPHPH  PGGQTPEPED
      human-beer.pro  CKCKRLTRFH  NQSELKDFGT  EAARPQKGRK  PRPRARSAKA  NQAELENAY- 301         314
    human-gremlin.pro  ----------  ----
   human-cerberus.pro  ----------  ----
       human-dan.pro  PPGAPHTEEE  GAED
      human-beer.pro  ----------  ----
```

*Fig. 1*

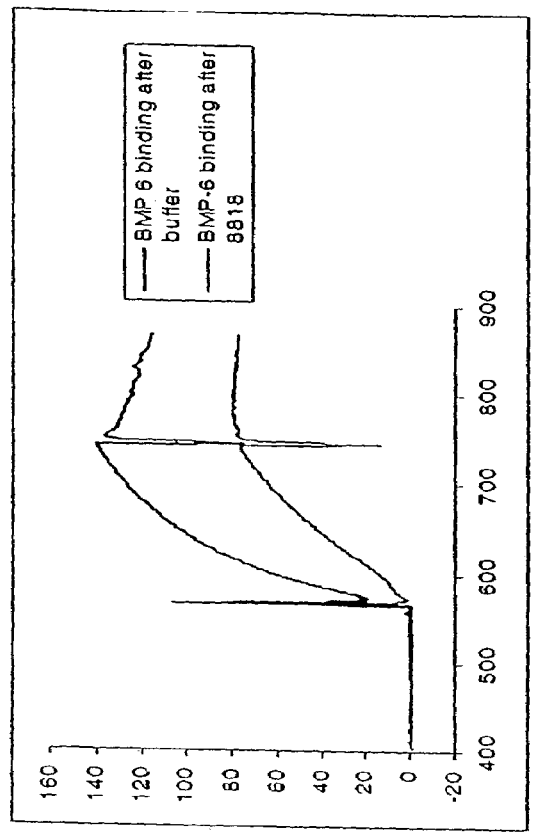
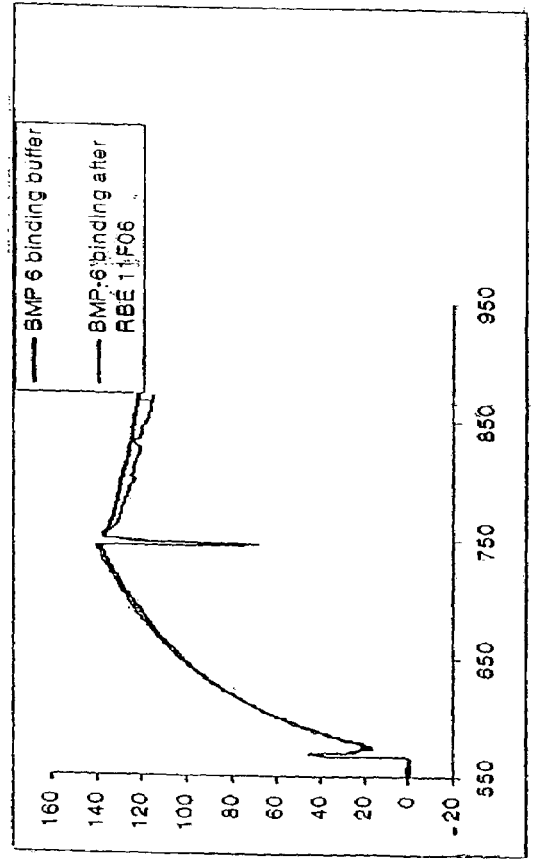
FIGURE 3

LIGANDS FOR TGF-BETA BINDING PROTEINS AND USES THEREOF

CROSS REFERENCE TO RELATED APPLICATION(S)

This application claims priority from U.S. Provisional Patent Application No. 60/455,253 filed Mar. 14, 2003.

BACKGROUND OF THE INVENTION

1. Field of the Invention

The present invention relates generally to pharmaceutical products and methods and, more specifically, to methods and compositions suitable for modulating (increasing or decreasing) the mineral content of bone. Such compositions and methods may be utilized to treat a wide variety of conditions, including for example, osteopenia, osteoporosis, fractures and other disorders in which low bone mineral density is a hallmark of the disease.

2. Description of the Related Art

Changes to bone mass occur in distinct phases over the life of an individual (e.g., Riggs, *West J. Med.* 154:63–77, 1991). The first phase occurs in both men and women, and proceeds to attainment of a peak bone mass. This first phase is achieved through linear growth of the endochondral growth plates, and radial growth due to a rate of periosteal apposition. The second phase begins around age 30 for trabecular bone (flat bones such as the vertebrae and pelvis) and about age 40 for cortical bone (e.g., long bones found in the limbs) and continues to old age. This phase is characterized by slow bone loss, and occurs in both men and women. In women, a third phase of bone loss also occurs, most likely due to postmenopausal estrogen deficiencies. During this phase alone, women may lose an additional 10% of bone mass from the cortical bone and 25% from the trabecular compartment (see Riggs, supra).

Loss of bone mineral content can be caused by a wide variety of conditions, and may result in significant medical problems. For example, osteoporosis is a debilitating disease in humans characterized by marked decreases in skeletal-bone mass and mineral density, structural deterioration of bone including degradation of bone microarchitecture and corresponding increases in bone fragility and susceptibility to fracture in afflicted individuals. Osteoporosis in humans is preceded by clinical osteopenia (bone mineral density that is greater than one standard deviation but less than 2.5 standard deviations below the mean value for young adult bone), a condition found in approximately 25 million people in the United States. Another 7–8 million patients in the United States have been diagnosed with clinical osteoporosis (defined as bone mineral content greater than 2.5 standard deviations below that of mature young adult bone). Osteoporosis is one of the most expensive diseases for the health care system, costing tens of billions of dollars annually in the United States. In addition to health care-related costs, long-term residential care and lost working days add to the financial and social costs of this disease. Worldwide approximately 75 million people are at risk for osteoporosis.

The frequency of osteoporosis in the human population increases with age, and among Caucasians osteoporosis is predominant in women (who comprise 80% of the osteoporosis patient pool in the United States). The increased fragility and susceptibility to fracture of skeletal bone in the aged is aggravated by the greater risk of accidental falls in this population. More than 1.5 million osteoporosis-related bone fractures are reported in the United States each year. Fractured hips, wrists, and vertebrae are among the most common injuries associated with osteoporosis. Hip fractures in particular are extremely uncomfortable and expensive for the patient, and for women correlate with high rates of mortality and morbidity.

Although osteoporosis has been regarded as an increase in the risk of fracture due to decreased bone mass, none of the presently available treatments for skeletal disorders can substantially increase the bone density of adults. There is a strong perception among many physicians that drugs are needed which could increase bone density in adults, particularly in the bones of the wrist, spinal column and hip that are at risk in osteopenia and osteoporosis.

Current strategies for the prevention of osteoporosis may offer some benefit to individuals but cannot ensure resolution of the disease. These strategies include moderate physical activity (particularly weight-bearing activities) with the onset of advanced age, including adequate calcium in the diet, and avoiding consumption of products containing alcohol or tobacco. For patients presenting with clinical osteopenia or osteoporosis, the prevalent current therapeutic drugs and strategies are directed to reducing further loss of bone mass by inhibiting the process of bone absorption, a natural component of the bone remodeling process that occurs constitutively.

For example, estrogen is now being prescribed to retard bone loss. There is, however, some controversy over whether there is any long term benefit to patients and whether there is any effect at all on patients over 75 years old. Moreover, use of estrogen is believed to increase the risk of breast and endometrial cancer. Calcitonin, osteocalcin with vitamin K, or high doses of dietary calcium, with or without vitamin D, have also been suggested for postmenopausal women. However, high doses of calcium can often have unpleasant gastrointestinal side effects, and serum and urinary calcium levels must be continuously monitored (e.g., Khosla and Rigss, *Mayo Clin. Proc.* 70:978–982, 1995).

Other therapeutic approaches to osteoporosis include bisphosphonates (e.g., Fosamax™, Actonel™, Bonviva™, Zometa™, olpadronate, neridronate, skelid, bonefos), parathyroid hormone, calcilytics, calcimimetics (e.g., cinacalcet), statins, anabolic steroids, lanthanum and strontium salts, and sodium fluoride. Such therapeutics however, are often associated with undesirable side effects (e.g., calcitonin and steroids may cause nausea and provoke an immune reaction, bisphosphonates and sodium fluoride may inhibit repair of fractures, even though bone density increases modestly) that may preclude their efficacious use (see Khosla and Rigss, supra).

Limited currently practiced therapeutic strategies for treating a condition associated with excessive or insufficient bone mineralization, such as osteoporosis or other disorders characterized by loss of bone mineralization, involves a drug that modulates (i.e., increases or decreases in a statistically significant manner) bone mass. In particular, no current strategy therapeutically stimulates or enhances the growth of new bone mass. The present invention provides compositions and methods which can be utilized to increase bone mineralization, and which therefore may be used to treat a wide variety of conditions where it is desirable to increase bone mass. The present invention also offers other related advantages.

BRIEF SUMMARY OF THE INVENTION

It is an aspect of the present invention to provide an isolated complex comprising a TGF-beta binding protein and a BMP antagonist protein in specific association, wherein (i) the TGF-beta binding protein comprises a sclerostin polypeptide that is capable of specifically binding a first TGF-beta superfamily member polypeptide that is selected from the group consisting of a BMP-5 polypeptide and a BMP-6 polypeptide, and (ii) the BMP antagonist protein is selected from the group consisting of a Chordin polypeptide and a Noggin polypeptide, said BMP antagonist protein being capable of specifically binding at least one second TGF-beta superfamily member polypeptide that is selected from the group consisting of a BMP-2 polypeptide, a BMP-4 polypeptide and a BMP-7 polypeptide, and wherein the complex is incapable of binding to the first TGF-beta superfamily member polypeptide.

The invention thus provides in certain embodiments an isolated complex comprising a first and a second TGF-beta binding protein in specific association, wherein; (a) the first TGF-beta binding protein is capable of binding a first TGF-beta superfamily member that is a first cognate ligand; and (b) the second TGF-beta binding protein is capable of binding a second TGF-beta superfamily member that is a second cognate ligand; wherein the complex is incapable of binding to the first cognate ligand.

In another embodiment the invention provides an isolated complex comprising a first and a second TGF-beta binding protein in specific association, wherein (a) the first TGF-beta binding protein is capable of binding a first TGF-beta superfamily member that is a first cognate ligand and (b) the second TGF-beta binding protein is capable of binding a second TGF-beta superfamily member that is a second cognate ligand; wherein the complex is incapable of binding to either of the first and second cognate ligands. In certain further embodiments the first TGF-beta binding protein comprises a sclerostin polypeptide and the first cognate ligand is at least one polypeptide selected from BMP-2, BMP-4, BMP-5, BMP-6 and BMP-7; and wherein the second TGF-beta binding protein comprises a chordin polypeptide and the second cognate ligand is a polypeptide selected from BMP 2, BMP4 and BMP-7. In certain other further embodiments the first TGF-beta binding protein comprises a sclerostin polypeptide and the first cognate ligand is a polypeptide selected from BMP-5 and BMP-6, and wherein the second TGF-beta binding protein comprises a noggin polypeptide and the second cognate ligand is a polypeptide selected from BMP-2, BMP-4, BMP-7, and GDF-5.

In another embodiments the present invention provides a method for identifying an agent that modulates binding between a TGF-beta binding protein and a BMP antagonist protein comprising the steps of (a) contacting, in the absence and presence of a candidate agent, a TGF-beta binding protein and a BMP antagonist protein under conditions and for a time sufficient to permit specific association of the TGF-beta binding protein and the BMP antagonist protein to form a complex according to claim 1; and (b) determining a level of complex that is present, wherein a difference in the level of complexes in the presence of the candidate agent relative to the level in the absence of the candidate agent indicates the agent modulates binding between the TGF-beta binding protein and the BMP antagonist protein In another embodiment there is provided a method for identifying an agent that modulates binding between a first TGF-beta binding protein and a second TGF-beta binding protein comprising the steps of (a) contacting, in the absence and presence of a candidate agent, a first and a second TGF-beta binding protein under conditions and for a time sufficient to permit specific association of the first and second TGF-beta binding proteins to form a complex; and (b) determining a level of complex that is present, wherein a difference in the level of complexes in the presence of the candidate agent relative to the level in the absence of the candidate agent indicates the agent alters binding between the first TGF-beta binding protein and the second TGF-beta binding protein.

In certain further embodiments of the two methods just described, the candidate agent decreases the specific association of proteins to form a complex, and in certain other further embodiments the candidate agent increases the specific association of proteins to form a complex, and in certain other further embodiments the candidate agent stabilizes the specific association of proteins to form a complex. In certain other further embodiments the candidate agent is selected from an organic molecule, a natural product, a peptide, an oligosacharride, a nucleic acid, a lipid, an antibody or binding fragment thereof, and a cell. In certain other further embodiments the candidate agent is obtained from a library of compounds, which library according to certain still further embodiments is selected from a random peptide library, a natural products library, a combinatorial library, an oligosaccharide library and a phage display library. Accordingly, it is an aspect of the invention to provide an agent identified according to any of the above described methods.

In certain other embodiments there is provided a method for modulating bone density comprising administering to a subject in need thereof an agent which modulates the interaction between (i) a sclerostin polypeptide that is capable of specifically binding a first TGF-beta superfamily member polypeptide that is selected from the group consisting of a BMP-5 polypeptide and a BMP-6 polypeptide, and (ii) a BMP antagonist protein that is selected from the group consisting of a Chordin polypeptide and a Noggin polypeptide, said BMP antagonist protein being capable of specifically binding at least one second TGF-beta superfamily member polypeptide that is selected from the group consisting of a BMP-2 polypeptide, a BMP-4 polypeptide and a BMP-7 polypeptide. In certain further embodiments the agent comprises a mimetic of the Chordin polypeptide or of the Noggin polypeptide. In certain other further embodiments the agent modulates bone mineralization.

These and other aspects of the present invention will become evident upon reference to the following detailed description and attached drawings. In addition, various references are set forth herein which describe in more detail certain aspects of this invention, and are therefore incorporated by reference in their entireties.

BRIEF DESCRIPTION OF THE SEVERAL VIEWS OF THE DRAWING(S)

FIG. 1 is a schematic illustration comparing the amino acid sequence of Human Dan; Human Gremlin; Human Cerberus and Human Beer. Arrows indicate the Cysteine backbone.

FIG. 3 shows binding of the BMP antagonist Noggin to sclerostin in an immunoprecipitation assay.

DETAILED DESCRIPTION OF THE INVENTION

Figure 2:
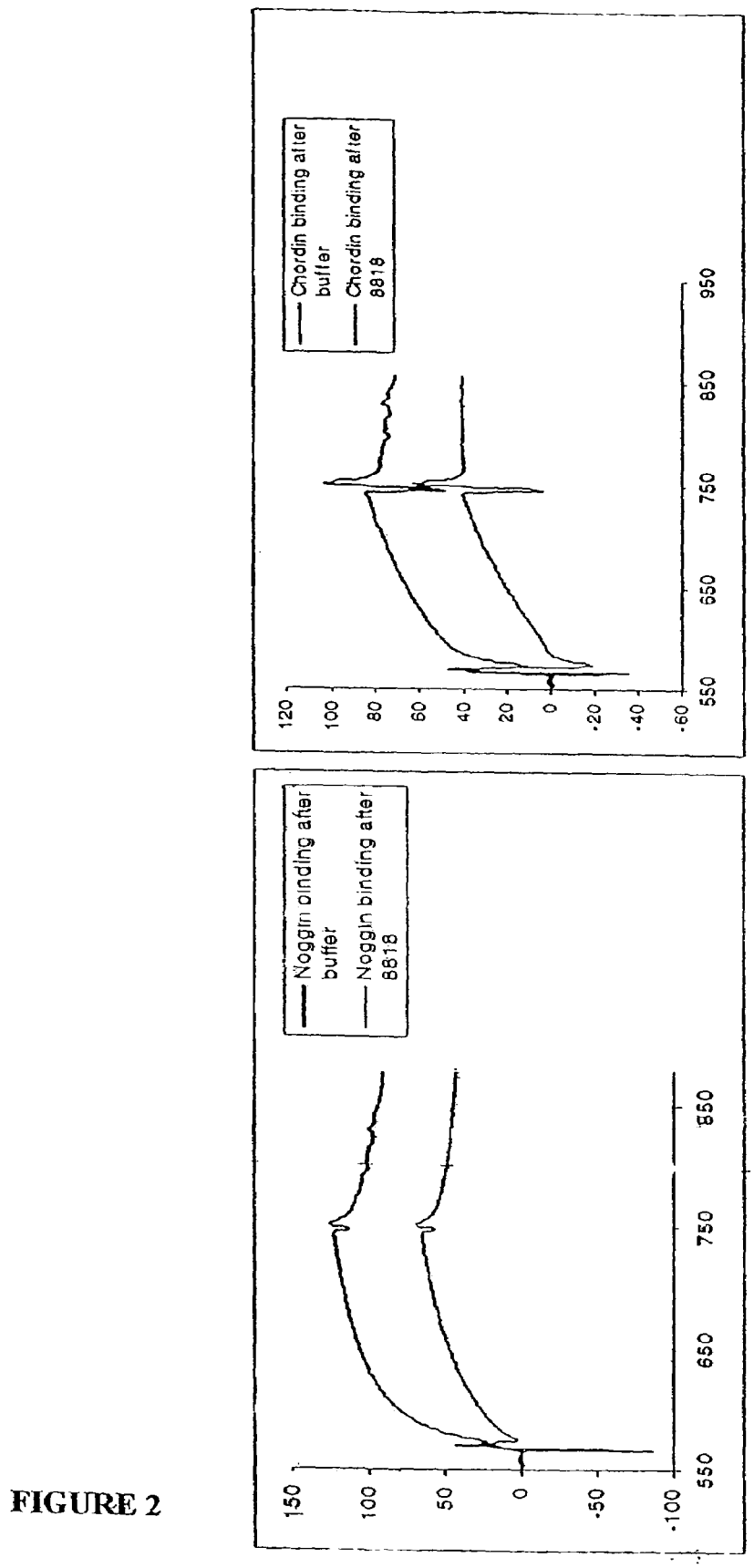
FIG. 2 shows binding of the BMP antagonists Chordin (FIG. 2A) and Noggin (FIG. 2B) to recombinant human sclerostin, as determined by surface plasmon resonance (SPR).

The present invention derives from the surprising observation of specific binding interactions between certain paired combinations of members of the extensive family of TGF-beta binding proteins with one another, instead of with members of the distinct TGF-beta superfamily of proteins, to form complexes of first and second TGF-beta binding proteins in specific association.

Accordingly and as described in greater detail below, according to certain aspects of the present invention there is identified for the first time an isolated complex comprising a TGF-beta binding protein and a BMP antagonist protein in specific association, wherein (i) the TGF-beta binding protein comprises a sclerostin polypeptide that is capable of specifically binding a first TGF-beta superfamily member polypeptide that is. selected from a BMP-5 polypeptide and a BMP-6 polypeptide, and (ii) the BMP antagonist protein is selected from a Chordin polypeptide and a Noggin polypeptide, the BMP antagonist protein being capable of specifically binding at least one second TGF-beta superfamily member polypeptide that is selected from a BMP-2 polypeptide, a BMP-4 polypeptide and a BMP-7 polypeptide, and wherein the complex is incapable of binding to the first TGF-beta superfamily member polypeptide.

The identification of such specific binding interactions between particular proteins provides binding pairs that may be usefully exploited, for example, to screen for agents that modulate (i.e., increase or decrease in a statistically significant manner) the formation of complexes by such proteins in specific association, which agents may be employed to manipulate physiological events mediated by the formation of such complexes. In particular, the compositions and methods provided by the present invention are useful in therapeutic strategies that relate to influencing bone mineralization, for instance in osteoporosis and other disorders associated with abnormal bone mineralization as described herein.

Molecules of particular interest according to the present invention should be understood to include proteins or peptides (e.g., antibodies, recombinant binding partners, peptides with a desired binding affinity), nucleic acids (e.g., DNA, RNA, chimeric nucleic acid molecules, and nucleic acid analogues such as PNA); and organic or inorganic compounds. Among especially significant molecules to which reference is made herein are Transforming Growth Factor-beta (TGF-beta), which includes any known or novel member of the TGF-beta super-family, which also includes bone morphogenic proteins (BMPs); TGF-beta receptors, which should be understood to refer to the receptor specific for a particular member of the TGF-beta super-family (including bone morphogenic proteins (BMPs)); and TGF-beta binding-proteins, which should be understood to refer to a protein with specific binding affinity for a particular member or subset of members of the TGF-beta super-family (including bone morphogenic proteins (BMPs)). Specific examples of TGF-beta binding-proteins include proteins encoded by SEQ ID NOs. 1, 5, 7, 9, 11, 13, and 15. (see, e.g., Balemans et al., 2002 Dev. Biol. 250:231; Schmitt et al., 1999 J. Orthopaed. Res. 17:269; Khalil, 1999 Microbes Infect. 1:1255; Miyazono et al., 1993 Growth Factors 8:11; von Bubnoff et al., 2001 Dev. Biol. 239:1; Koli et al., 2001 Microsc. Res. Tech. 52:354; Ebara et al., 2002 Spine 27(16 Suppl. 1):S10; Bondestam, 2002, Ligands & Signaling Components of the Transforming Growth Factor βFamily, Helsinki University Biomedical Dissertations No. 17). Accordingly, for example, inhibiting the binding of the TGF-beta binding-protein to the TGF-beta family of proteins and bone morphogenic proteins (BMPs) should be understood to refer to molecules which allow the activation of TGF-beta or bone morphogenic proteins (BMPs), or allow the binding of TGF-beta family members including bone morphogenic proteins (BMPs) to their respective receptors, by removing or preventing TGF-beta from binding to TGF-binding-protein. Such inhibition may be accomplished, for example, by molecules which inhibit the binding of the TGF-beta binding-protein to specific members of the TGF-beta superfamily.

Vector refers to an assembly which is capable of directing the expression of desired protein. The vector must include transcriptional promoter elements which are operably linked to the gene(s) of interest. The vector may be composed of either deoxyribonucleic acids ("DNA"), ribonucleic acids ("RNA"), or a combination of the two (e.g., a DNA-RNA chimeric). Optionally, the vector may include a polyadenylation sequence, one or more restriction sites, as well as one or more selectable markers such as neomycin phosphotransferase or hygromycin phosphotransferase. Additionally, depending on the host cell chosen and the vector employed, other genetic elements such as an origin of replication, additional nucleic acid restriction sites, enhancers, sequences conferring inducibility of transcription, and selectable markers, may also be incorporated into the vectors described herein.

An isolated nucleic acid molecule is a nucleic acid molecule that is not integrated in the genomic DNA of an organism. For example, a DNA molecule that encodes a TGF-binding protein that has been separated from the genomic DNA of a eukaryotic cell is an isolated DNA molecule. Another example of an isolated nucleic acid molecule is a chemically-synthesized nucleic acid molecule that is not integrated in the genome of an organism. The isolated nucleic acid molecule may be genomic DNA, cDNA, RNA, or composed at least in part of nucleic acid analogs.

An isolated polypeptide is a polypeptide that is essentially free from contaminating cellular components, such as carbohydrate, lipid, or other proteinaceous impurities associated with the polypeptide in nature. Within certain embodiments, a particular protein preparation contains an isolated polypeptide if it appears nominally as a single band on SDS-PAGE gel with Coomassie Blue staining. "Isolated" when referring to organic molecules means that the compounds are greater than 90 percent pure utilizing methods which are well known in the art (e.g., NMR, melting point).

Sclerosteosis is a term that was applied by Hansen (1967) (Hansen, H. G., Sklerosteose.In: Opitz, H.; Schmid, F., Handbuch der Kinderheilkunde. Berlin: Springer (pub.) 6 1967. Pp. 351–355) to a disorder similar to van Buchem hyperostosis corticalis generalisata but possibly differing in radiologic appearance of the bone changes and in the presence of asymmetric cutaneous syndactyly of the index and middle fingers in many cases. The jaw has an unusually square appearance in this condition.

Humanized antibodies are recombinant proteins in which donor (such as murine, rabbit) complementarity determining regions of monoclonal antibodies have been transferred from heavy and light variable chains of the donor immunoglobulin into an acceptor (such as human) variable domain. As used herein, an antibody fragment is a portion of an antibody such as F(ab')$_2$, F(ab)$_2$, Fab', Fab, and the like. Regardless of structure, an antibody fragment binds with the same antigen that is recognized by the intact antibody. For example, an anti-TGF-beta binding-protein monoclonal antibody fragment binds with an epitope of TGF-beta binding-protein.

The term antibody fragment also includes any synthetic or genetically engineered protein that acts like an antibody by binding to a specific antigen to form a complex. For example, antibody fragments include isolated fragments consisting of the light and heavy chain variable region, "Fv" fragments consisting of the variable regions of the heavy and light chains, recombinant single chain polypeptide molecules in which light and heavy variable regions are connected by a peptide linker ("sFv proteins"), and minimal recognition units consisting of the amino acid residues that mimic the hypervariable region.

Fv is the minimum antibody fragment that contains a complete antigen recognition and binding site. This region consists of a dimer of one heavy and one light chain variable domain in a tight, non-covalent association (VH-VL dimer). It is in this configuration that the three CDRs of each variable domain interact to define an antigen binding site on the surface of the VH-VL dimer. Collectively, the six CDRs confer antigen binding specificity to the antibody. However, even a single variable domain (or half of an Fv comprising only three CDRs specific for an antigen) has the ability to recognize and bind antigen, although at a lower affinity than the entire binding site.

Single chain antibody ("SCA"), defined as a genetically engineered molecule containing the variable region of the light chain, the variable region of the heavy chain, linked by a suitable polypeptide linker as a genetically fused single chain molecule. Such single chain antibodies are also referred to as "single-chain Fv" or "sFv" antibody fragments. Generally, the Fv polypeptide further comprises a polypeptide linker between the VH and VL domains that enables the sFv to form the desired structure for antigen binding. For a review of sFv see Pluckthun in The Pharmacology of Monoclonal Antibodies, vol. 113, Rosenburg and Moore eds. Springer-Verlag, N.Y., pp. 269–315 (1994).

The term "diabodies" refers to a small antibody fragments with two antigen-binding sites, which fragments comprise a heavy chain variable domain (VH) connected to a light chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies and similar small antibody constructs are described more fully in, for example, EP 404,097; WO 93/11161, Hollinger et al., Proc. Natl. Acad. Sci. USA 90: 6444–6448 (1993); Muyldermaus, S., J. Biotechnol., 74:277–302 (2001); Davies, J. et al., Biotechnology, 13:475–479 (1995); Nguyen, V. K. et al., Immunology, 109:93–101 (2003).

A detectable label is a molecule or atom which can be conjugated to an antibody moiety to produce a molecule useful for diagnosis. Examples of detectable labels include chelators, photoactive agents, radioisotopes, fluorescent agents, paramagnetic ions, enzymes, and other marker moieties.

As used herein, an immunoconjugate is a molecule comprising an anti-TGF-beta binding-protein antibody, or an antibody fragment, and a detectable label. An immunoconjugate has roughly the same, or only slightly reduced, ability to bind TGF-beta binding-protein after conjugation as before conjugation.

As used herein to modulate means to increase or decrease in a statistically significant manner.

Abbreviations: TGF-beta—"Transforming Growth Factor-beta"; TGF-bBP—"Transforming Growth Factor-beta binding-protein" (one representative TGF-bBP is designated "sclerostin", "Beer" or "H. Beer"); BMP—"bone morphogenic protein"; PCR—"polymerase chain reaction"; RT-PCR—PCR process in which RNA is first transcribed into DNA at the first step using reverse transcriptase (RT); cDNA—any DNA made by copying an RNA sequence into DNA form.

As noted above, the present invention provides isolated complexes comprising a TGF-beta binding protein in specific association with a BMP antagonist protein, and related methods and compositions including those for increasing bone mineral content in warm-blooded animals. Briefly, the present inventions are based upon the unexpected discovery that the BMP antagonist proteins chordin and noggin are each able to bind specifically to sclerostin. Thus, as discussed in more detail below this discovery has led to the development of assays which may be utilized to select molecules which inhibit the binding of the TGF-beta binding-protein to the TGF-beta family of proteins and bone morphogenic proteins (BMPs), and methods of utilizing such molecules for increasing the bone mineral content of warm-blooded animals (including for example, humans).

The Transforming Growth Factor-beta (TGF-beta) super-family contains a variety of growth factors that share common sequence elements and structural motifs (at both the secondary and tertiary levels). This protein family is known to exert a wide spectrum of biological responses on a large variety of cell types. Many of them have important functions during the embryonal development in pattern formation and tissue specification; in adults they are involved, e.g., in wound healing and bone repair and bone remodeling, and in the modulation of the immune system. In addition to the three TGF-beta's, the super-family includes the Bone Morphogenic Proteins (BMPs), Activins, Inhibins, Growth and Differentiation Factors (GDFs), and Glial-Derived Neurotrophic Factors (GDNFs). Primary classification is established through general sequence features that bin a specific protein into a general sub-family. Additional stratification within the sub-family is possible due to stricter sequence conservation between members of the smaller group. In certain instances, such as with BMP-5, BMP-6 and BMP-7, this can be as high as 75 percent amino acid homology between members of the smaller group. This level of identity enables a single representative sequence to illustrate the key biochemical elements of the sub-group that separates it from other members of the larger family.

TGF-beta signals by inducing the formation of heterooligomeric complexes of type I and type II receptors. The crystal structure of TGF-beta2 has been determined. The general fold of the TGF-beta2 monomer contains a stable, compact, cysteine knotlike structure formed by three disulphide bridges. Dimerization, stabilized by one disulphide bridge, is antiparallel.

TGF-beta family members initiate their cellular action by binding to receptors with intrinsic serine/threonine kinase activity. This receptor family consists of two subfamilies, denoted type I and type II receptors. Each member of the TGF-beta family binds to a characteristic combination of type I and type II receptors, both of which are needed for signaling. In the current model for TGF-beta receptor activation, TGF-beta first binds to the type II receptor (TbR-II), which occurs in the cell membrane in an oligomeric form with activated kinase. Thereafter, the type I receptor (TbR-I), which can not bind ligand in the absence of TbR-II, is recruited into the complex. TbR-II then phosphorylates TbR-I predominantly in a domain rich in glycine and serine residues (GS domain) in the juxtamembrane region, and thereby activates TbR-I.

Bone Morphogenic Proteins (BMPs) are Key Regulatory Proteins in Determining Bone Mineral Density in Humans. A major advance in the understanding of bone formation was the identification of the bone morphogenic proteins (BMPs), also known as osteogenic proteins (OPs), which regulate cartilage and bone differentiation in vivo. BMPs/OPs induce endochondral bone differentiation through a cascade of events which include formation of cartilage, hypertrophy and calcification of the cartilage, vascular invasion, differentiation of osteoblasts, and formation of bone. As described above, the BMPs/OPs (BMP 2–14, and osteogenic protein 1 and -2, OP-1 and OP-2) are members of the TGF-beta super-family. The striking evolutionary conservation between members the BMP/OP sub-family suggests that they are critical in the normal development and function of animals. Moreover, the presence of multiple forms of BMPs/OPs raises an important question about the biological relevance of this apparent redundancy. In addition to posf-fetal chondrogenesis and osteogenesis, the BMPs/OPs play multiple roles in skeletogenesis (including the development of craniofacial and dental tissues) and in embryonic development and organogenesis of parenchymatous organs, including the kidney. It is now understood that nature relies on common (and few) molecular mechanisms tailored to provide the emergence of specialized tissues and organs. The BMP/OP super-family is an elegant example of nature parsimony in programming multiple specialized functions deploying molecular isoforms with minor variation in amino acid motifs within highly conserved carboxy-terminal regions.

The BMP and Activin sub-families are subject to significant post-translational regulation. An intricate extracellular control system exists, whereby a high affinity antagonist is synthesized and exported, and subsequently complexes selectively with BMPs or activins to disrupt their biological activity (W. C. Smith (1999) TIG 15(1) 3–6). A number of these natural antagonists have been identified, and based on sequence divergence appear to have evolved independently due to the lack of primary sequence conservation. There has been no structural work to date on this class of proteins. Studies of these antagonists has highlighted a distinct preference for interacting and neutralizing BMP-2 and BMP-4. Furthermore, the mechanism of inhibition seems to differ for the different antagonists (S. Iemura et al. (1998) *Proc Natl Acad Sci USA* 95 9337–9342).

U.S. Pat. Nos. 6,395,511, 6,489,445 and 6,495,736 provide sclerostin, also known as Beer proteins, a novel class of TGF-beta binding-proteins that possess a nearly identical cysteine (disulfide) scaffold when compared to Human DAN, Human Gremlin, and Human Cerberus, and SCGF (U.S. Pat. No. 5,780,263) but almost no homology at the nucleotide level (for background information, see generally Hsu, D. R., Economides, A. N.; Wang, X., Eimon, P. M., Harland, R. M., "The *Xenopus* Dorsalizing Factor Gremlin Identifies a Novel Family of Secreted Proteins that Antagonize BMP Activities," *Molecular Cell* 1:673–683, 1998).

One representative example of the novel class of TGF-beta binding-proteins is disclosed in SEQ ID NOs:1, 5, 9, 11, 13, and 15. Representative members of this class of binding proteins should also be understood to include variants of the TGF-beta binding-protein (e.g., SEQ ID NOs:5 and 7). As utilized herein, a "TGF-beta binding-protein variant gene" refers to nucleic acid molecules that encode a polypeptide having an amino acid sequence that is a modification of SEQ ID NOs: 2, 10, 12, 14 or 16. Such variants include naturally-occurring polymorphisms or allelic variants of TGF-beta binding-protein genes, as well as synthetic genes that contain conservative amino acid substitutions of these amino acid sequences. Additional variant forms of a TGF-beta binding-protein gene are nucleic acid molecules that contain insertions or deletions of the nucleotide sequences described herein. TGF-beta binding-protein variant genes can be identified by determining whether the genes hybridize with a nucleic acid molecule having the nucleotide sequence of SEQ ID NOs: 1, 5, 7, 9, 11, 13, or 15 under stringent conditions. In addition, TGF-beta binding-protein variant genes should encode a protein having a cysteine backbone.

As an alternative, TGF-beta binding-protein variant genes can be identified by sequence comparison. As used herein, two amino acid sequences have "100% amino acid sequence identity" if the amino acid residues of the two amino acid sequences are the same when aligned for maximal correspondence. Similarly, two nucleotide sequences have "100% nucleotide sequence identity" if the nucleotide residues of the two nucleotide sequences are the same when aligned for maximal correspondence. Sequence comparisons can be performed using standard software programs such as those included in the LASERGENE bioinformatics computing suite, which is produced by DNASTAR (Madison, Wisconsin). Other methods for comparing two nucleotide or amino acid sequences by determining optimal alignment are well-known to those of skill in the art (see, for example, Peruski and Peruski, *The Internet and the New Biology: Tools for Genomic and Molecular Research* (ASM Press, Inc. 1997), Wu et al. (eds.), "Information Superhighway and Computer Databases of Nucleic Acids and Proteins," in Methods in Gene Biotechnology, pages 123–151 (CRC Press, Inc. 1997), and Bishop (ed.), Guide to Human Genome Computing, 2nd Edition (Academic Press, Inc. 1998)).

A variant TGF-beta binding-protein should have at least a 50% amino acid sequence identity to SEQ ID NOs: 2, 6, 10, 12, 14 or 16 and preferably, greater than 60%, 65%, 70%, 75%, 80%, 85%, 90%, or 95% identity. Alternatively, TGF-beta binding-protein variants can be identified by having at least a 70% nucleotide sequence identity to SEQ ID NOs: 1, 5, 9, 11, 13 or 15. Moreover, the present invention contemplates TGF-beta binding-protein gene variants having greater than 75%, 80%, 85%, 90%, or 95% identity to SEQ ID NO:1. Regardless of the particular method used to identify a TGF-beta binding-protein variant gene or variant TGF-beta binding-protein, a variant TGF-beta binding-protein or a polypeptide encoded by a variant TGF-beta binding-protein gene can be functionally characterized by, for example, its ability to bind to and/or inhibit the signaling of a selected member of the TGF-beta family of proteins, or by its ability to bind specifically to an anti-TGF-beta binding-protein antibody.

The present invention includes functional fragments of TGF-beta binding-protein genes. Within the context of this invention, a "functional fragment" of a TGF-beta binding-protein gene refers to a nucleic acid molecule that encodes a portion of a TGF-beta binding-protein polypeptide which either (1) possesses the above-noted function activity, or (2)

specifically binds with an anti-TGF-beta binding-protein antibody. For example, a functional fragment of a TGF-beta binding-protein gene described herein comprises a portion of the nucleotide sequence of SEQ ID NOs: 1, 5, 9, 11, 13, or 15.

Chordin (e.g., Reddi et al. 2001 *Arthritis Research* 3:1; Oelgeschlager et al., 2000 Nature 405:757), cystine knot proteins such as noggin (e.g., Groppe et al., 2002 *Nature* 420:636), and the distinct DAN family of proteins (including DAN, Cerberus and Gremlin; e.g., Hsu et al., 1998 *Mol. Cell* 1:673) represent three general classifications of secreted BMP antagonist proteins that act extracellularly (e.g., Balemans et al., 2002 *Dev. Biol.* 250:231). Amino acid sequence alignment of human sclerostin (Beer) with Cerberus, DAN and Gremlin showed that despite a highly similar cysteine scaffold among the four proteins, sclerostin otherwise exhibited little homology with the DAN family members (FIG. 1; see also U.S. Pat. No. 6,395,511). Examples of noggin, chordin and BMP polypeptides that may be used according to certain embodiments of the present invention are listed according to Genbank/NCBI Accession Numbers in Table 1.

TABLE 1

Representative TGF-beta Binding Proteins/
BMP Antagonist Proteins/BMPs

| Source | Chordin | Noggin | BMP-5 | BMP-6 |
|---|---|---|---|---|
| Human | XM_209529, AF209928, AX235836, AF283325, AF209930, AF209929, BC002909, AX175126, AX175126, AX175123, AX140204, AX140203, AX140202, AX140201, AX140200, AX140199, AX140198, AX140197, AX140196, AX140195, AF136632S4, AF136634, AF136633, AF136632, AH009297, AF076612, | | NM_021073, M60314 | NM_001718 |
| Mouse | AK077460, AK007577, NM_009893, AX235833, AX175120, AX140205, AF096276, AF069501 | | NM_007555, L41145, L02240 | NM_007556, AH003686, U73520, U73519, U73518, U73517, U73516, U73515 |
| Rabbit | AB073105 | | AF412307 | |
| Rat | NW_042725, XM_221307, AB073715, D86581 | | XM_236415 | AY184240, XM_214455 |
| Chicken | AF031230 | | S83278 | |
| Sheep | AY150846 | | | AF508310 |
| Goat | | | | |
| Xenopus laevis | L35764, | | | |
| Horse | | | | AF510665 |
| Zebra-Fish | NM_130973, AF034606, AR063998, AR063997 18203652 18202942 25140444 1072455 18202071 2498235 2498234 18858413 6753418 16555891 2731578 11494125 16215740 15077351 7839323 7839322 7839321 7839320 4406186 1468951 3822218 3800772 2826739 603945 11494373 (Alternative Splice Form) 11494129 (Alternative Splice Form) 11494127 (Alternative Splice Form) | 214626 285271 1117817 1117819 1352511 1710365 3695029 3860047 4185744 4432769 4885523 5410599 5410601 7110675 15214085 15214097 15214098 15214099 15214132 15214133 15214136 15214137 18859109 18859111 18859113 21105761 21707595 21907883 27374944 | | |

Antibody Compositions, Fragments Thereof and Other Binding Agents According to another aspect, the present invention further provides binding agents, such as antibodies and antigen-binding fragments thereof, that are capable of detecting the complexes described herein, or are capable of modulating the formation of the complexes described herein, and/or are capable of modulating one or more aspects of bone density.

For example in one illustrative embodiment, the binding agents bind to a complex formed between Sclerostin (Beer) and either Chordin or Noggin. Such binding agents may be used, for example, in the detection of the complexes described herein, and hence are useful in the detection of additional compounds that bind to a complex formed between Sclerostin (Beer) and Noggin or between Sclerostin (Beer) and Chordin. Alternatively, or in addition, binding agents of the present invention may be targeted, for example, to regions of Sclerostin (Beer), Noggin, and/or Chordin identified as responsible for the binding interactions between these proteins. Such binding agents can accordingly be used for disrupting the formation of complexes between Sclerostin (Beer) and Chordin or Sclerostin (Beer) and Noggin and in this way may be useful for modulating bone density.

In one illustrative embodiment, the binding agent is an antibody or an antigen-binding fragment thereof. Antibodies may be prepared by any of a variety of techniques known to those of ordinary skill in the art. See, e.g., Harlow and Lane, *Antibodies: A Laboratory Manual*, Cold Spring Harbor Laboratory, 1988. In general, antibodies can be produced by cell culture techniques, including the generation of monoclonal antibodies as described herein, or via transfection of antibody genes into suitable bacterial or mammalian cell hosts, in order to allow for the production of recombinant antibodies. In one technique, an immunogen comprising the polypeptide is initially injected into any of a wide variety of mammals (e.g., mice, rats, rabbits, sheep or goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support. The mammal used to elicit an immune response to the immunogen may be a knock-out mammal. In this embodiment, gene knock-out methods known in the art are used to raise animals that do not naturally express the protein corresponding to the immunogen. Knock-out technology is well-known in the art and is disclosed in, for example, U.S. Pat. Nos. 6,252,132; 6,437,215; and 6,444,873.

Monoclonal antibodies specific for an antigenic polypeptide of interest may be prepared, for example, using the technique of Kohler and Milstein, *Eur. J. Immunol.* 6:511–19, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

A number of "humanized" antibody molecules comprising an antigen-binding site derived from a non-human immunoglobulin have been described, including chimeric antibodies having rodent V regions and their associated CDRs fused to human constant domains (Winter et al., *Nature* 349:293–99, 1991; Lobuglio et al., *Proc. Nat. Acad. Sci. USA* 86:4220–24, 1989; Shaw et al., *J. Immunol.* 138:4534–38, 1987; and Brown et al., *Cancer Res.* 47:3577–83, 1987), rodent CDRs grafted into a human supporting FR prior to fusion with an appropriate human antibody constant domain (Riechmann et al., *Nature* 332: 323–27, 1988; Verhoeyen et al., *Science* 239:1534–36, 1988; and Jones et al., *Nature* 321:522–25, 1986), and rodent CDRs supported by recombinantly veneered rodent FRs (European Patent Publication No. 519,596, published Dec. 23, 1992). These "humanized" molecules are designed to minimize unwanted immunological response toward rodent antihuman antibody molecules which limits the duration and effectiveness of therapeutic applications of those moieties in human recipients.

The invention therefore contemplates human and humanized forms of non-human (e.g. murine) antibodies. Such humanized antibodies are chimeric immunoglobulins, immunoglobulin chains or fragments thereof (such as Fv, Fab, Fab', F(ab')2 or other antigen-binding subsequences of antibodies) that contain minimal sequence derived from non-human immunoglobulin. For the most part, humanized antibodies are human immunoglobulins (recipient antibody) in which residues from a complementary determining region (CDR) of the recipient are replaced by residues from a CDR of a nonhuman species (donor antibody) such as mouse, rat or rabbit having the desired specificity, affinity and capacity. Thus, Fv framework residues of the human immunoglobulin can be replaced by corresponding non-human residues. Furthermore, humanized antibodies may comprise residues that are found neither in the recipient antibody nor in the imported CDR or framework sequences. These modifications are made to further refine and optimize antibody performance. In general, humanized antibodies will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin. (Reichmann et al., Nature 332, 323–329 (1988); Presta, Curr. Op. Struct. Biol. 2, 593–596 (1992); Holmes, et al., J. Immunol., 158:2192–2201 (1997) and Vaswani, et al., Annals Allergy, Asthma & Immunol., 81:105–115 (1998).)

The invention also provides methods of mutating antibodies to optimize their affinity, selectivity, binding strength or other desirable property. A mutant antibody refers to an amino acid sequence variant of an antibody. In general, one or more of the amino acid residues in the mutant antibody is different from what is present in the reference antibody. Such mutant antibodies necessarily have less than 100% sequence identity or similarity with the reference amino acid sequence. In general, mutant antibodies have at least 75% amino acid sequence identity or similarity with the amino acid sequence of either the heavy or light chain variable domain of the reference antibody. Preferably, mutant antibodies have at least 80%, more preferably at least 85%, even more preferably at least 90%, and most preferably at least 95% amino acid sequence identity or similarity with the amino acid sequence of either the heavy or light chain variable domain of the reference antibody. One method of mutating antibodies involves affinity maturation using phage display.

As used herein, the terms "veneered FRs" and "recombinantly veneered FRs" refer to the selective replacement of FR residues from, e.g., a rodent heavy or light chain V region, with human FR residues in order to provide a xenogeneic molecule comprising an antigen-binding site which retains substantially all of the native FR polypeptide folding structure. Veneering techniques are based on the understanding that the ligand binding characteristics of an antigen-binding site are determined primarily by the structure and relative disposition of the heavy and light chain CDR sets within the antigen-binding surface. Davies et al., *Ann. Rev. Biochem.* 59:439–73, 1990. Thus, antigen binding specificity can be preserved in a humanized antibody only wherein the CDR structures, their interaction with each other, and their interaction with the rest of the V region domains are carefully maintained. By using veneering techniques, exterior (e.g., solvent-accessible) FR residues which are readily encountered by the immune system are selectively replaced with human residues to provide a hybrid molecule that comprises either a weakly immunogenic, or substantially non-immunogenic veneered surface.

The process of veneering makes use of the available sequence data for human antibody variable domains compiled by Kabat et al., in *Sequences of Proteins of Immunological Interest*, 4th ed., (U.S. Dept. of Health and Human Services, U.S. Government Printing Office, 1987), updates to the Kabat database, and other accessible U.S. and foreign databases (both nucleic acid and protein). Solvent accessibilities of V region amino acids can be deduced from the known three-dimensional structure for human and murine antibody fragments. There are two general steps in veneering a murine antigen-binding site. Initially, the FRs of the variable domains of an antibody molecule of interest are compared with corresponding FR sequences of human variable domains obtained from the above-identified sources. The most homologous human V regions are then compared residue by residue to corresponding murine amino acids. The residues in the murine FR which differ from the human counterpart are replaced by the residues present in the human moiety using recombinant techniques well known in the art. Residue switching is only carried out with moieties which are at least partially exposed (solvent accessible), and care is exercised in the replacement of amino acid residues which may have a significant effect on the tertiary structure of V region domains, such as proline, glycine and charged amino acids.

In this manner, the resultant "veneered" murine antigen-binding sites are thus designed to retain the murine CDR residues, the residues substantially adjacent to the CDRs, the residues identified as buried or mostly buried (solvent inaccessible), the residues believed to participate in non-covalent (e.g., electrostatic and hydrophobic) contacts between heavy and light chain domains, and the residues from conserved structural regions of the FRs which are believed to influence the "canonical" tertiary structures of the CDR loops. These design criteria are then used to prepare recombinant nucleotide sequences which combine the CDRs of both the heavy and light chain of a murine antigen-binding site into human-appearing FRs that can be used to transfect mammalian cells for the expression of recombinant human antibodies which exhibit the antigen specificity of the murine antibody molecule.

The invention also contemplates partially or fully human antibodies specific for an antigenic polypeptide of interest. Such antibodies may be prepared using methods known in the art, such as described in Lonberg, N. et al., Int. Rev. Immunol., 13:65–93 (1995); Fishwild, D. M. et al., Nat. Biotechnol., 14:826 (1996); U.S. Pat. No. 6,632,976 B1 to Tomizuka et al.; and Tomizuka, K. et al., Proc. Nat'l. Acad. Sci., 97:722–727 (2000) (describing fully human antibodies). Antigen-binding fragments of human antibodies prepared as described above are also contemplated.

In another embodiment of the invention, monoclonal antibodies of the present invention may be coupled to one or more therapeutic agents. Suitable agents in this regard include radionuclides, differentiation inducers, drugs, toxins, and derivatives thereof. Preferred radionuclides include $^{90}Y$, $^{123}I$, $^{125}I$, $^{131}I$, $^{186}Re$, $^{188}Re$, $^{211}At$, and $^{212}Bi$. Preferred drugs include methotrexate, and pyrimidine and purine analogs. Preferred differentiation inducers include phorbol esters and butyric acid. Preferred toxins include ricin, abrin, diptheria toxin, cholera toxin, gelonin, Pseudomonas exotoxin, Shigella toxin, and pokeweed antiviral protein.

A therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers that provide multiple sites for attachment can be used. Alternatively, a carrier can be used.

A carrier may bear the agents in a variety of ways, including covalent bonding either directly or via a linker group. Suitable carriers include proteins such as albumins (e.g., U.S. Pat. No. 4,507,234, to Kato et al.), peptides and polysaccharides such as aminodextran (e.g., U.S. Pat. No. 4,699,784, to Shih et al.). A carrier may also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562, to Davison et al. discloses representative chelating compounds and their synthesis.

Assays for Selecting Molecules Which Increase Bone Density: Screening for Compounds that Mediate Effects On Bone Density Essentially any type of compound may be tested according to the methods described herein using any suitable screening procedure, such as a high throughput screening assay. Accordingly, the examples of compounds and screening techniques described below are offered for purposes of illustration only. Illustrative test compounds for use in the screening methods described herein can include, but are not limited to, antibodies, antigens, nucleic acids (e.g., natural or synthetic DNA, RNA, gDNA, cDNA, mRNA, tRNA, RNAi, etc.), lectins, sugars, oligosaccharides, glycoproteins, receptors, growth factors, cytokines, small molecules such as drug candidates (from, for example, a random peptide library, a natural products library, a legacy library, a combinatorial library, an oligosaccharide library and a phage display library), metabolites, enzyme substrates, enzyme inhibitors, enzyme co-factors such as vitamins, lipids, steroids, metals, oxygen and other gases found in physiologic fluids, cells, cellular constituents, cell membranes and associated structures, cell adhesion molecules, natural products found in plant and animal sources, other partially or completely synthetic products, and the like.

As noted above, according to one illustrative embodiment of the present invention, methods are provided for identifying a compound that modulates the binding of Noggin or Chordin to Sclerostin (Beer). Such methods involve first providing a composition comprising Sclerostin (Beer) and either Noggin or Chordin under conditions wherein said Sclerostin (Beer) binds either Noggin or Chordin with a predetermined binding affinity. The Noggin or Chordin polypeptide used according to this embodiment can comprise an isolated polypeptide containing the entire Noggin or Chordin protein, and preferably comprises at least the domain of Noggin or Chordin that binds to Sclerostin (Beer). In addition, the Sclerostin (Beer) polypeptide used in this embodiment can comprise an isolated polypeptide containing the entire Sclerostin (Beer) protein, and preferably comprises at least the domain of Sclerostin (Beer) that binds to either Noggin or Chordin.

In the context of the screening methods of the present invention, the formation of a complex between Sclerostin (Beer) and either Noggin or Chordin, can be detected or measured directly or indirectly using any suitable method. For example, one or more of the polypeptides disclosed herein can be labeled with a suitable label and the formation of a complex can be determined by detection of the label. Labels suitable for use in detection of a complex between either Noggin or Chordin and Sclerostin (Beer) can include, for example, a radioisotope, an epitope label (tag), an affinity label (e.g., biotin, avidin), a spin label, an enzyme, a fluorescent group, chemiluminescent group, and the like. When labels are not employed, complex formation can be determined, for example, using any other technique known in the art, illustrative examples of which include cross-linking, co-immunoprecipitation and co-fractionation by chromatography, and the yeast two-hybrid system.

The composition comprising one of the above described compositions of either Noggin or Chordin and Sclerostin (Beer) is contacted with a test compound in order to determine whether the test compound is capable of modulating the binding between Sclerostin (Beer) and either Noggin or Chordin. By comparing the binding affinity determined in the presence of a test compound with, for example, the binding affinity between either Noggin or Chordin and Sclerostin (Beer) in the absence of the test compound, the method allows for the identification of test compounds capable of modulating the interaction between these proteins.

According to still another aspect of the invention, there is provided a method for identifying a compound that modulates, and preferably inhibits, the binding of either Noggin or Chordin with Sclerostin (Beer). Again, by comparing the binding affinity determined in the presence of a test compound with, for example, the binding affinity between either Noggin or Chordin and Sclerostin (Beer) in the absence of the test compound, the method identifies whether the test compound is capable of inhibiting the interaction between these proteins.

According to still another aspect of the invention, there is provided a method for identifying a compound that modulates, and preferably enhance, the binding of either Noggin or Chordin with Sclerostin (Beer). Again, by comparing the binding affinity determined in the presence of a test compound with, for example, the binding affinity between either Noggin or Chordin and Scierostin (Beer) in the absence of the test compound, the method identifies whether the test compound is capable of enhancing the interaction between these proteins.

In another embodiment, the level of Sclerostin (Beer) binding to either Noggin or Chordin in the presence of a test compound is compared with the level Sclerostin (Beer) binding to either Noggin or Chordin in the absence of said test compound. In certain illustrative embodiments of the current invention, the level of binding in the presence of the test compound is decreased by, for example, 100%, 90%, 80%, 75%, 70%, or 50%, or less, compared to cells not exposed to the test compound.

In another embodiment, the level of Sclerostin (Beer) binding to either Noggin or Chordin in the presence of a test compound is compared with the level of Sclerostin (Beer) binding to either Noggin or Chordin in the absence of said test compound. In certain illustrative embodiments of the current invention, the level of binding in the presence of the test compound is increased by, for example, 100%, 90%, 80%, 75%, 70%, or 50%, or less, compared to cells not exposed to the test compound.

According to still another aspect of the present invention, there are provided compounds identified by any of the above methods.

In addition to the illustrative assays described above for the screening of test compounds, any of a variety of molecular libraries can be employed in conjunction with the screening methods of the present invention. Libraries are intentionally created collections of different molecules which are prepared using, for example, organic synthetic methods, biochemical methods and others. In the latter case, the molecules can be made in vitro or in vivo. Such libraries include, for example, random peptide libraries, combinatorially synthesized libraries, phage display libraries, natural product libraries, oligosaccharide libraries and legacy libraries (a collection of molecules synthesized over time and collected).

A significant development in pharmaceutical drug discovery and design has been the development of combinatorial chemistry to create chemical libraries of potential new drugs. Chemical libraries are intentionally created collections of different molecules, made, for example, by organic synthetic methods or biochemically. Combinatorial chemistry is a synthetic strategy in which the chemical members of the library are made according to a systematic methodology by the assembly of chemical subunits. Each molecule in the library is thus made up of one or more of these subunits. The chemical subunits may include naturally-occurring or modified amino acids, naturally-occurring or modified nucleotides, naturally-occurring or modified saccharides or other molecules, whether organic or inorganic. Typically, each subunit has at least two reactive groups, permitting the stepwise construction of larger molecules by reacting first one then another reactive group of each subunit to build successively more complex and potentially diverse molecules.

By creating synthetic conditions whereby a fixed number of individual building blocks, for example, the twenty naturally-occurring amino acids, are made equally available at each step of the synthesis, a very large array or library of compounds can be assembled after even a few steps of the synthesis reaction. Using amino acids as an example, at the first synthetic step the number of resulting compounds (N) is equal to the number of available building blocks, designated as b. In the case of the naturally-occurring amino acids, b=20. In the second step of the synthesis, assuming that each amino acid has an equal opportunity to form a dipeptide with every other amino acid, the number of possible compounds $N=b^2=20^2=400$.

For successive steps of the synthesis, again assuming random, equally efficient assembly of the building blocks to the resulting compounds of the previous step, $N=b^x$ where x equals the number of synthetic assembly steps. Thus, it can be seen that for random assembly of only a decapeptide the number of different compounds is $20^{10}$ or $1.02 \times 10^{13}$. Such an extremely large number of different compounds permits the assembly and screening of a large number of diverse candidates for the ability to modulate LDLR2-mediated HIV infection.

Biologically synthesized combinatorial libraries have been constructed using techniques of molecular biology in bacteria or bacteriophage particles. For example, U.S. Pat. Nos. 5,270,170 and 5,338,665 to Schatz describe the construction of a recombinant plasmid encoding a fusion protein created through the use of random oligonucleotides inserted into a cloning site of the plasmid. This cloning site is placed within the coding region of a gene encoding a DNA binding protein, such as the lac repressor, so that the specific binding function of the DNA binding protein is not destroyed upon expression of the gene. The plasmid also contains a nucleotide sequence recognized as a binding site by the DNA binding protein. Thus, upon transformation of a suitable bacterial cell and expression of the fusion protein, the protein will bind the plasmid which produced it. The bacterial cells are then lysed and the fusion proteins assayed for a given biological activity. Moreover, each fusion protein remains associated with the nucleic acid which encoded it; thus through nucleic acid amplification and sequencing of the nucleic acid portion of the protein:plasmid complexes which are selected for further characterization, the precise structure of the candidate compound can be determined. The Schatz patents are incorporated herein by reference.

Similarly, bacteriophage display libraries have been constructed through cloning random oligonucleotides within a portion of a gene encoding one or more of the phage coat proteins. Upon assembly of the phage particles, the random polypeptides also face outward for screening. As in the previously described system, the phage particles contain the nucleic acid encoding the fusion protein, so that nucleotide sequence information identifying the drug candidate is linked to the drug itself. Such phage expression libraries are described in, for example, Sawyer et al., *Protein Engineering* 4:947–53, 1991; Akamatsu et al., *J. Immunol.* 151: 4651–59, 1993, and Dower et al., U.S. Pat. No. 5,427,908. These patents and publications are incorporated herein by reference.

Other approaches to creating molecularly diverse combinatorial libraries employ chemical synthetic methods to make use of atypical or non-biological building blocks in the assembly of the compounds to be tested. Thus, Zuckermann et al., *J. Med. Chem.* 37:2678–85, 1994, describe the construction of a library using a variety of N-(substituted) glycines for the synthesis of peptide-like compounds termed "peptoids." The substitutions were chosen to provide a series of aromatic substitutions, a series of hydroxylated side substitutions, and a diverse set of substitutions including branched, amino, and heterocyclic structures. This publication is incorporated by reference herein.

Another strategy involves chemically synthesizing the combinatorial libraries on solid supports in a methodical and predetermined fashion, so that the placement of each library member gives information concerning the synthetic structure of that compound. Examples of such methods are described, for example, in Geysen, U.S. Pat. No. 4,833,092, in which compounds are synthesized on functionalized polyethylene pins designed to fit a 96 well microtiter dish so that the position of the pin gives the researcher information as to the compound's structure. Similarly Hudson et al., PCT Publication No. WO94/05394, describe methods for the construction of combinatorial libraries of biopolymers, such as polypeptides, oligonucleotides and oligosaccharides, on a spatially addressable solid phase plate coated with a functionalized polymer film. In this system the compounds are synthesized and screened directly on the plate. Knowledge of the position of a given compound on the plate yields information concerning the nature and order of building blocks comprising the compound. Similar methods of constructing addressable combinatorial libraries may be used for the synthesis of compounds other than biopolymers.

Still another illustrative approach has been the use of large numbers of very small derivatized beads, which are divided into as many equal portions as there are different building blocks. In the first step of the synthesis, each of these portions is reacted with a different building block. The beads are then thoroughly mixed and again divided into the same number of equal portions. In the second step of the synthesis each portion, now theoretically containing equal amounts of each building block linked to a bead, is reacted with a different building block. The beads are again mixed and separated, and the process is repeated as desired to yield a large number of different compounds, with each bead containing only one type of compound.

This methodology, termed the "one-bead one-compound" method, yields a mixture of beads with each bead potentially bearing a different compound. Thus, in this method the beads themselves cannot be considered "addressable" in the same sense as in the solid phase supports and arrays described above, or as in the cellular or phage libraries. However, the compounds displayed in the surface of each bead can be tested for the ability to bind with a specific compound, and, if those (typically) few beads are able to be identified and separated from the other beads, a presumable pure population of compounds can be recovered and analyzed. Of course, this latter possibility depends upon the ability to load and extract enough information concerning the compounds on the surface of each bead to be susceptible to meaningful subsequent analysis. Such information may simply be in the form of an adequate amount of the compound of interest to be able to determine its structure. For example, in the case of a peptide, enough of the peptide must be synthesized on the bead to be able to perform peptide sequencing and obtain the amino acid sequence of the peptide.

As described above, the construction of combinatorial libraries allows one to screen a vast number of test compounds for the ability to modulate Sclerostin (Beer) binding to either Noggin or Chordin.

One common screening method currently applied consists of coating a solid support, such as the wells of a microtiter dish, with the specific molecule for which a binding partner is sought. The library member compounds are then labeled, plated onto the solid support, and allowed to bind the library members. After a wash step, the binding partner complexes are then detected by detection of the label joined to the bound library members. This type of procedure is particularly well suited to combinatorial libraries wherein the member compounds are provided in a solution or medium. This method can be somewhat labor-intensive and, in order to achieve the high throughput required to screen such large numbers of test compounds, may as a first step require screening pools of test compounds, followed by one or more rescreening step in order to specifically identify the compound of interest. The situation can also be reversed, so that the library members are allowed to coat individual wells and are probed with the specific molecule.

In cases wherein the combinatorial library is to contain antibody analogs or peptides targeted to a given epitope, the library members may contain a portion of an antibody recognized by a secondary antibody able to be detected, for example in an enzyme-linked immunological assay (ELISA) or by virtue of being directly or indirectly labeled, for example with a radionuclide, a chemiluminescent compound, a fluor, and enzyme or dye.

Tawfik et al., *Proc. Natl. Acad. Sci.* 90:373–77, 1993, describe a method of screening a library of antibodies (in this case, from a hybridoma library generated using a mimic of the transition state intermediate of an enzymatic reaction) for the presence of rare antibodies having a desired catalytic activity. The screening compound, in this case the enzyme substrate, was immobilized on 96 well microtiter dishes. Supernatants from each clone were placed into separate wells under conditions promoting the enzymatic reaction. The products of the enzymatic reaction, still immobilized to the microtiter dish, were assayed by the use of product-specific monoclonal antibodies. Again, this type of screening process is quite labor-intensive and may necessitate repetitive screening of pools of test compounds in order to achieve high throughput of large libraries.

In the cellular or phage display libraries and "one-bead one-compound" synthetic libraries described above the library members can be screened for the ability to bind a specific binding partner (e.g., a receptor) which is labeled with a detectable fluor, such as fluorescein or phycoerythrin. Because each particle (for example, a cell or a bead) displays only one species of test compound, the fluorescently labeled particles can be detected and sorted using a fluorescence activated cell sorter (FACS). An enriched population of positive beads or particles can then be rescreened, if necessary, and individually analyzed. This strategy can be employed using cells displaying the test compounds or beads on which the test compounds are synthesized.

Certain methods of the present invention utilize arrays to conduct the screening process. The use of arrays makes it possible to greatly increase sample throughput. Structurally, the array is typically formed on a solid support that includes multiple elements or sites. In the screening methods of the present invention, each element of the array includes a signal path such as a transmission line to which a protein target or ligand is electromagnetically coupled or directly attached. In many screening tests, the goal is to screen a large number of compounds against one protein target. Thus, in such methods, all the protein targets located within any element, as well as all the targets at different elements, are the same. Each element is contacted with different samples, each sample containing a different compound. In this way, it is possible to screen the different compounds in a library with a common target.

In other methods, however, it may be desirable for all the protein targets in any particular element to be the same, but for the protein targets in different elements to vary from one another. This allows one test ligand or group of ligands to be screened against several different protein targets. So, for example, assuming ten different protease inhibitors are used as targets, the array would preferably include ten rows or columns of elements, each element having a different protease.

Regardless of the identity of the targets at the various array elements, a signal is launched down the signal path running to each element to monitor binding at each of the various elements. Modulations in the launched signal are used to detect binding between the target and a ligand in the sample. An array may be used in conjunction with a microfluidic device to controllably add microquantities of different samples to the different arrays. In the situation in which all the targets are identical, typically the fluidic device is used to dispense different samples to the various arrays; whereas, when the protein target in the various elements vary, the fluidic device dispenses the same sample to the different elements of the arrays.

Some methods utilize arrays synthesized on a solid support as described above. In certain methods, it is possible to focus the screening process towards ligands more likely to have a desired biological activity by utilizing the sequence of a ligand known to bind to the protein target of interest (a "lead sequence") to inform the selection of sequences synthesized on the array to be used in subsequent rounds of screening. See, for example, U.S. Pat. No. 5,770,456, which is incorporated herein by reference in its entirety. Thus, a series of ligands related to the lead sequence are synthesized by making systematic variations at one or more positions of the lead sequence. The theory is that minor alterations of a sequence (e.g., a peptide) known to bind a target protein may result in a sequence with even higher binding affinity.

The number of elements in an array varies widely, based primarily on the type of screening application for which the array is to be used. In the initial stages of screening of a library, for example, a large number of elements are preferred so that a large number of compounds can quickly be screened. Arrays for such applications can have up to $10^6$ elements. In other instances, there are up to $10^3$ elements in the array. In yet other methods, there may only be a single element, such as when it is desired to conduct higher resolution studies with a compound that appears from initial rounds of screening to be a good candidate for a lead compound having potential therapeutic value. Hence, in general, the number of elements in the array can be 1, 10, $10^2$, $10^3$, $10^4$, $10^5$, or $10^6$, or any number or range therebetween.

The density of the protein target or ligands that make up the array can also vary significantly. The density required varies on various factors such as the degree of signal sensitivity, the number of ligands in solution and whether characteristic peaks for a particular complex under study are well-defined and are resolved from signals from other complexes. In the optimal situation, the sensitivity of the present system and the ability to conduct analyses using signals known to be correlated with certain complexes means that an element may contain a single protein target or ligand. In other situations, however, the density of protein targets or ligands may be up to 100 targets/cm$^2$. In still other, methods, the density may be up to $10^8$ targets/cm$^2$, up to $10^{12}$ targets/cm$^2$ and up to $10^{18}$ targets/cm$^2$.

It is possible through the use or array and microfluidic technology to use the methods described herein in a high throughput screening process (HTS). In such an approach, hundreds of thousands of compounds are screened for their ability to bind a particular target or screened according to the higher levels of analysis described above. For example, the invention described herein can be miniaturized, so that highly parallel screening platforms can be realized; platforms which are capable of screening hundreds or thousands of compounds simultaneously, and at the same time determining the effect of binding (e.g., agonist or antagonist), affinity, kinetics, etc As discussed above, the present invention provides methods for selecting and/or isolating compounds which are capable of increasing bone density. For example, within one aspect of the present invention methods are provided for determining whether a selected molecule is capable of increasing bone mineral content, comprising the steps of (a) mixing a selected molecule with TGF-beta binding protein and a selected member of the TGF-beta family of proteins, (b) determining whether the selected molecule stimulates signaling by the TGF-beta family of proteins, or inhibits the binding of the TGF-beta binding protein to the TGF-beta family of proteins. Within certain embodiments, the molecule enhances the ability of TGF-beta to function as a positive regulator of mesenchymal cell differentiation.

Within other aspects of the invention, methods are provided for determining whether a selected molecule is capable of increasing bone mineral content, comprising the steps of (a) exposing a selected molecule to cells which express TGF-beta binding-protein and (b) determining whether the activity (or expression) of TGF-beta binding-protein from the exposed cells decreases, and therefrom determining whether the compound is capable of increasing bone mineral content. Within one embodiment, the cells are selected from the group consisting of the spontaneously transformed or untransformed normal human bone from bone biopsies and rat parietal bone osteoblasts. Such methods may be accomplished in a wide variety of assay formats including, for example, Countercurrent Immuno-Electrophoresis (CIEP), Radioimmunoassays, Radioimmunoprecipitations, Enzyme-Linked Immuno-Sorbent Assays (ELISA), Dot Blot assays, Inhibition or Competition assays, and sandwich assays (see U.S. Pat. Nos. 4,376,110 and 4,486,530; see also *Antibodies: A Laboratory Manual*, supra).

Representative embodiments of such assays are provided in U.S. Pat. No. 6,395,511. Briefly, a family member of the TGF-beta super-family or a TGF-beta binding protein is first bound to a solid phase, followed by addition of a candidate molecule. The labeled family member of the TGF-beta super-family or a TGF-beta binding protein is then added to the assay, the solid phase washed, and the quantity of bound or labeled TGF-beta super-family member or TGF-beta binding protein on the solid support determined. Molecules which are suitable for use in increasing bone mineral content as described herein are those molecules which decrease the binding of TGF-beta binding protein to a member or members of the TGF-beta super-family in a statistically significant manner. Assays suitable for use within the present invention need not be limited to the embodiments described herein and in U.S. Pat. No. 6,395,511. In particular, numerous parameters may be altered, such as by binding TGF-beta to a solid phase, or by elimination of a solid phase entirely.

Within other aspects of the invention, methods are provided for determining whether a selected molecule is capable of increasing bone mineral content, comprising the steps of (a) exposing a selected molecule to cells which express TGF-beta and (b) determining whether the activity of TGF-beta from the exposed cells is modulated, and therefrom determining whether the compound is capable of increasing bone mineral content. Similar to the above described methods, a wide variety of methods may be utilized to assess the changes of TGF-beta binding-protein expression due to a selected test compound.

For example, within one aspect of the present invention methods are provided for determining whether a selected molecule is capable of increasing bone mineral content, comprising the steps of (a) mixing a selected molecule with TGF-beta-binding-protein and a selected member of the TGF-beta family of proteins, (b) determining whether the selected molecule up-regulates the signaling of the TGF-beta family of proteins, or inhibits the binding of the TGF-beta binding-protein to the TGF-beta family of proteins. Within certain embodiments, the molecule enhances the ability of TGF-beta to function as a positive regulator of mesenchymal cell differentiation.

Similar to the above described methods, a wide variety of methods may be utilized to assess stimulation of TGF-beta due to a selected test compound. One such representative method is provided below in U.S. Pat. No. 6,395,511. (see also Durham et al., *Endo*. 136:1374–1380).

Within yet other aspects of the present invention, methods are provided for determining whether a selected molecule is capable of increasing bone mineral content, comprising the step of determining whether a selected molecule inhibits the binding of TGF-beta binding-protein to bone, or an analogue thereof. As utilized herein, it should be understood that bone or analogues thereof refers to hydroxyapatite, or a surface composed of a powdered form of bone, crushed bone or intact bone. Similar to the above described methods, a wide variety of methods may be utilized to assess the inhibition of TGF-beta binding-protein localization to bone matrix. One such representative method is described in U.S. Pat. No. 6,395,511.

It should be noted that while the methods recited herein may refer to the analysis of an individual test molecule, that the present invention should not be so limited. In particular, the selected molecule may be contained within a mixture of compounds. Hence, the recited methods may further comprise the step of isolating a molecule which inhibits the binding of TGF-beta binding-protein to a TGF-beta family member.

Pharmaceutical Compositions In additional embodiments, the present invention concerns formulation of one or more of the polynucleotide, polypeptide, antibody, antisense or other compositions disclosed herein, in pharmaceutically-acceptable carriers for use in the assays described herein and/or in the administration of a composition to a cell or an animal, either alone, or in combination with one or more other modalities of therapy.

It will be understood that, if desired, a composition as disclosed herein may be administered in combination with other agents as well, such as, e.g., other proteins or polypeptides or various pharmaceutically-active agents. In fact, there is virtually no limit to other components that may also be included, given that the additional agents do not cause a significant adverse effect upon contact with the target cells or host tissues. The compositions may thus be delivered along with various other agents as required in the particular instance. Such compositions may be purified from host cells or other biological sources, or alternatively may be chemically synthesized as described herein. Likewise, such compositions may further comprise substituted or derivatized RNA or DNA compositions.

Therefore, in another aspect of the present invention, pharmaceutical compositions are provided comprising one or more of the polynucleotide, polypeptide and/or antibody compositions described herein in combination with a physiologically acceptable carrier.

While any suitable carrier known to those of ordinary skill in the art may be employed in the pharmaceutical compositions of this invention, the type of carrier will typically vary depending on the mode of administration. Compositions of the present invention may be formulated for any appropriate manner of administration, including for example, topical, oral, nasal, mucosal, intravenous, intracranial, intraperitoneal, subcutaneous and intramuscular administration.

Carriers for use within such pharmaceutical compositions are biocompatible, and may also be biodegradable. In certain embodiments, the formulation preferably provides a relatively constant level of active component release. In other embodiments, however, a more rapid rate of release immediately upon administration may be desired. The formulation of such compositions is well within the level of ordinary skill in the art using known techniques. Illustrative carriers useful in this regard include microparticles of poly(lactide-co-glycolide), polyacrylate, latex, starch, cellulose, dextran and the like. Other illustrative delayed-release carriers include supramolecular biovectors, which comprise a non-liquid hydrophilic core (e.g., a cross-linked polysaccharide or oligosaccharide) and, optionally, an external layer comprising an amphiphilic compound, such as a phospholipid (see e.g., U.S. Pat. No. 5,151,254 and PCT applications WO 94/20078, WO/94/23701 and WO 96/06638). The amount of active compound contained within a sustained release formulation depends upon the site of implantation, the rate and expected duration of release and the nature of the condition to be treated or prevented.

In another illustrative embodiment, biodegradable microspheres (e.g., polylactate polyglycolate) are employed as carriers for the compositions of this invention. Suitable biodegradable microspheres are disclosed, for example, in U.S. Pat. Nos. 4,897,268; 5,075,109; 5,928,647; 5,811,128; 5,820,883; 5,853,763; 5,814,344, 5,407,609 and 5,942,252. Modified hepatitis B core protein carrier systems, such as described in WO/99 40934, and references cited therein, will also be useful for many applications. Another illustrative carrier/delivery system employs a carrier comprising particulate-protein complexes, such as those described in U.S. Pat. No. 5,928,647, which are capable of inducing a class I-restricted cytotoxic T lymphocyte responses in a host.

In another illustrative embodiment, calcium phosphate core particles are employed as carriers or as controlled release matrices for the compositions of this invention. Exemplary calcium phosphate particles are disclosed, for example, in published patent application No. WO/0046147.

The pharmaceutical compositions of the invention will often further comprise one or more buffers (e.g., neutral buffered saline or phosphate buffered saline), carbohydrates (e.g., glucose, mannose, sucrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives. Alternatively, compositions of the present invention may be formulated as a lyophilizate.

The development of suitable dosing and treatment regimens for using the particular compositions described herein in a variety of treatment regimens, including e.g., oral, parenteral, intravenous, intranasal, and intramuscular administration and formulation, is well known in the art, some of which are briefly discussed below for general purposes of illustration.

In certain applications, the pharmaceutical compositions disclosed herein may be delivered via oral administration to an animal. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain circumstances it will be desirable to deliver the pharmaceutical compositions disclosed herein parenterally, intravenously, intramuscularly, or even intraperitoneally. Such approaches are well known to the skilled artisan, some of which are further described, for example, in U.S. Pat. No. 5,543,158; U.S. Pat. No. 5,641,515 and U.S. Pat. No. 5,399,363. In certain embodiments, solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations generally will contain a preservative to prevent the growth of microorganisms.

Illustrative pharmaceutical forms suitable for injectable use include sterile aqueous solutions or dispersions and sterile powders for the extemporaneous preparation of sterile injectable solutions or dispersions (for example, see U.S. Pat. No. 5,466,468). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and/or by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

In one embodiment, for parenteral administration in an aqueous solution, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, *Remington's Pharmaceutical Sciences*, 15th ed., pp. 1035–1038 and 1570–1580). Some variation in dosage will necessarily occur depending on the condition of the subject being treated. Moreover, for human administration, preparations will of course preferably meet sterility, pyrogenicity, and the general safety and purity standards as required by FDA Office of Biologics standards.

In another embodiment of the invention, the compositions disclosed herein may be formulated in a neutral or salt form. Illustrative pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective.

The carriers can further comprise any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. The phrase "pharmaceutically-acceptable" refers to molecular entities and compositions that do not produce an allergic or similar untoward reaction when administered to a human.

In certain embodiments, liposomes, nanocapsules, microparticles, lipid particles, vesicles, and the like, are used for the introduction of the compositions of the present invention into suitable host cells/organisms. In particular, the compositions of the present invention may be formulated for delivery either encapsulated in a lipid particle, a liposome, a vesicle, a nanosphere, or a nanoparticle or the like. Alternatively, compositions of the present invention can be bound, either covalently or non-covalently, to the surface of such carrier vehicles.

The formation and use of liposome and liposome-like preparations as potential drug carriers is generally known to those of skill in the art (see for example, Lasic, *Trends Biotechnol.* 16(7):307–21, 1998; Takakura, *Nippon Rinsho* 56(3):691–95, 1998; Chandra n et al., *Indian J. Exp. Biol.* 35(8):801–09, 1997; Margalit, *Crit. Rev. Ther. Drug Carrier Syst* 12(2–3):233–61, 1995; U.S. Pat. No. 5,567,434; U.S. Pat. No. 5,552,157; U.S. Pat. No. 5,565,213; U.S. Pat. No. 5,738,868 and U.S. Pat. No. 5,795,587, each specifically incorporated herein by reference in its entirety).

Liposomes have been used successfully with a number of cell types that are normally difficult to transfect by other procedures, including T cell suspensions, primary hepatocyte cultures and PC 12 cells (Renneisen et al., *J. Biol. Chem.* 265(27):16337–42, 1990; Muller et al., *DNA Cell Biol.* 9(3):221–29, 1990). In addition, liposomes are free of the DNA length constraints that are typical of viral-based delivery systems. Liposomes have been used effectively to introduce genes, various drugs, radiotherapeutic agents, enzymes, viruses, transcription factors, allosteric effectors and the like, into a variety of cultured cell lines and animals. Furthermore, he use of liposomes does not appear to be associated with autoimmune responses or unacceptable toxicity after systemic delivery.

In certain embodiments, liposomes are formed from phospholipids that are dispersed in an aqueous medium and spontaneously form multilamellar concentric bilayer vesicles (also termed multilamellar vesicles (MLVs).

Alternatively, in other embodiments, the invention provides for pharmaceutically-acceptable nanocapsule formulations of the compositions of the present invention. Nanocapsules can generally entrap compounds in a stable and reproducible way (see, for example, Quintanar-Guerrero et al., *Drug Dev. Ind. Pharm.* 24(12):1113–28, 1998). To avoid side effects due to intracellular polymeric overloading, such ultrafine particles (sized around 0.1 μm) may be designed using polymers able to be degraded in vivo. Such particles can be made as described, for example, by Couvreur et al., *Crit. Rev. Ther. Drug Carrier Syst.* 5(1):1–20, 1988; zur Muhlen et al., *Eur J. Pharm. Biopharm.* 45(2):149–55, 1998; Zambaux et al., *J. Controlled Release* 50(1–3):31–40, 1998; and U.S. Pat. No. 5,145,684.

Methods of Treatment The present invention also provides methods for increasing the mineral content and mineral density of bone. Briefly, numerous conditions result in the loss of bone mineral content, including for example, disease, genetic predisposition, accidents which result in the lack of use of bone (e.g., due to fracture), therapeutics which effect bone resorption, or which kill bone forming cells and normal aging. Through use of the molecules described herein which inhibit the TGF-beta binding-protein binding to a TGF-beta family member such conditions may be treated or prevented. As utilized herein, it should be understood that bone mineral content has been increased, if bone mineral content has been increased in a statistically significant manner (e.g., greater than one-half standard deviation), at a selected site.

A wide variety of conditions which result in loss of bone mineral content may be treated with the molecules described herein. Patients with such conditions may be identified through clinical diagnosis utilizing well known techniques (see, e.g., Harrison's Principles of Internal Medicine, McGraw-Hill, Inc.). Representative examples of diseases that may be treated included dysplasias, wherein there is abnormal growth or development of bone. Representative examples of such conditions include achondroplasia, cleidocranial dysostosis, enchondromatosis, fibrous dysplasia, Gaucher's, hypophosphatemic rickets, Marfan's, multiple hereditary exotoses, neurofibromatosis, osteogenesis imperfecta, osteopetrosis, osteopoikilosis, sclerotic lesions, fractures, periodontal disease, pseudoarthrosis and pyogenic osteomyelitis.

Other conditions which may be treated or prevented include a wide variety of causes of osteopenia (i.e., a condition that causes greater than one standard deviation of bone mineral content or density below peak skeletal mineral content at youth). Representative examples of such conditions include anemic states, conditions caused steroids, conditions caused by heparin, bone marrow disorders, scurvy, malnutrition, calcium deficiency, idiopathic osteoporosis, congenital osteopenia or osteoporosis, alcoholism, chronic liver disease, senility, postmenopausal state, oligomenorrhea, amenorrhea, pregnancy, diabetes mellitus, hyperthyroidism, Cushing's disease, acromegaly, hypogonadism, immobilization or disuse, reflex sympathetic dystrophy syndrome, transient regional osteoporosis and osteomalacia. Other conditions include inflammatory conditions associated with bone loss, such as rheumatoid arthritis.

Within one aspect of the present invention, bone mineral content or density may be increased by administering to a warm-blooded animal a therapeutically effective amount of a molecule which inhibits the TGF-beta binding-protein binding to a TGF-beta family member. Examples of warm-blooded animals that may be treated include both vertebrates and mammals, including for example humans, horses, cows, pigs, sheep, dogs, cats, rats and mice. Representative examples of therapeutic molecules include ribozymes, ribozyme genes, antisense oligonucleotides and antibodies (e.g., humanized antibodies).

Within other aspects of the present invention, methods are provided for increasing bone density, comprising the step of introducing into cells which home to bone a vector which directs the expression of a molecule which inhibits the TGF-beta binding-protein binding to a member of the TGF-beta family, and administering the vector containing cells to a warm-blooded animal. Briefly, cells which home to bone may be obtained directly from the bone of patients (e.g., cells obtained from the bone marrow such as CD34+, osteoblasts, osteocytes, and the like), from peripheral blood, or from cultures.

A vector which directs the expression of a molecule that inhibits the TGF-beta binding-protein binding to a member of the TGF-beta family is introduced into the cells. Representative examples of suitable vectors include viral vectors such as herpes viral vectors (e.g., U.S. Pat. No. 5,288,641), adenoviral vectors (e.g., WO 94/26914, WO 93/9191; Kolls etal., *PNAS* 91(1):215–219, 1994; Kass-Eisler et al., *PNAS* 90(24):11498–502, 1993; Guzman et al., *Circulation* 88(6): 2838–48, 1993; Guzman et al., *Cir. Res.* 73(6):1202–1207, 1993; Zabner et al., *Cell* 75(2):207–216, 1993; Li et al., *Hum Gene Ther.* 4(4):403–409, 1993; Caillaud et al., *Eur. J. Neurosci.* 5(10:1287–1291, 1993; Vincent et al., *Nat. Genet.* 5(2):130–134, 1993; Jaffe et al., *Nat. Genet.* 1(5):372–378, 1992; and Levrero et al., *Gene* 101(2):195–202, 1991), adeno-associated viral vectors (WO 95/13365; Flotte et al., *PNAS* 90(22): 10613–10617, 1993), baculovirus vectors, parvovirus vectors (Koering et al., *Hum. Gene Therap.* 5:457–463, 1994), pox virus vectors (Panicali and Paoletti, *PNAS* 79:4927–4931, 1982; and Ozaki et al., *Biochem. Biophys. Res. Comm.* 193(2):653–660, 1993), and retroviruses (e.g., EP 0,415,731; WO 90/07936; WO 91/0285, WO 94/03622; WO 93/25698; WO 93/25234; U.S. Pat. No. 5,219,740; WO 93/11230; WO 93/10218). Viral vectors may likewise be constructed which contain a mixture of different elements (e.g., promoters, envelope sequences and the like) from different viruses, or non-viral sources. Within various embodiments, either the viral vector itself, or a viral particle which contains the viral vector may be utilized in the methods and compositions described below.

Within other embodiments of the invention, nucleic acid molecules which encode a molecule which inhibits the TGF-beta binding-protein binding to a member of the TGF-beta family themselves may be administered by a variety of techniques, including, for example, administration of asialoosomucoid (ASOR) conjugated with poly-L-lysine DNA complexes (Cristano et al., *PNAS* 92122–92126, 1993), DNA linked to killed adenovirus (Curiel et al., *Hum. Gene Ther.* 3(2):147–154, 1992), cytofectin-mediated introduction (DMRIE-DOPE, Vical, Calif.), direct DNA injection (Acsadi et al., *Nature* 352:815–818, 1991); DNA ligand (Wu et al., *J. of Biol. Chem.* 264:16985–16987, 1989); lipofection (Felgner et al., *Proc. Natl. Acad. Sci. USA* 84:7413–7417, 1989); liposomes (Pickering et al., *Circ.* 89(1):13–21, 1994; and Wang et al., *PNAS* 84:7851–7855, 1987); microprojectile bombardment (Williams et al., *PNAS* 88:2726–2730, 1991); and direct delivery of nucleic acids which encode the protein itself either alone (Vile and Hart, *Cancer Res.* 53: 3860–3864, 1993), or utilizing PEG-nucleic acid complexes.

Representative examples of molecules which may be expressed by the vectors of present invention include ribozymes and antisense molecules, each of which are discussed in more detail above.

Determination of increased bone mineral content may be determined directly through the use of X-rays (e.g., Dual Energy X-ray Absorptometry or "DEXA"), or by inference through bone turnover markers (osteoblast specific alkaline phosphatase, osteocalcin, type 1 procollagen C' propeptide (PICP), and total alkaline phosphatase; see Comier, C., *Curr. Opin. in Rheu.* 7:243, 1995), or markers of bone resorption (pyridinoline, deoxypryridinoline, N-telopeptide, urinary hydroxyproline, plasma tartarate-resistant acid phosphatases and galactosyl hydroxylysine; see Comier, supra). The amount of bone mass may also be calculated from body weights, or utilizing other methods (see Guinness-Hey, *Metab. Bone Dis. and Rel. Res.* 5:177–181, 1984).

As will be evident to one of skill in the art, the amount and frequency of administration will depend, of course, on such factors as the nature and severity of the indication being treated, the desired response, the condition of the patient, and so forth. Typically, the compositions may be administered by a variety of techniques, as noted above.

The following Examples are offered by way of illustration and not limitation.

EXAMPLES

Example 1

Identification of Ligands for TGF-Beta Binding Proteins

Polypeptide sequences for TGF-beta binding polypeptides known as scierostin or Beer proteins have been previously described, as have polynucleotides encoding such polypeptides, and related compositions and methods for preparing isolated recombinant sclerostin or Beer proteins (e.g., U.S. Pat. Nos. 6,395,511; 6,489,445; 6,495,736). Sclerostin ("Beer") protein binding interactions with the TGF-beta superfamily members BMP-5 and BMP-6 were previously demonstrated as described above.

This Example describes the demonstration of specific association in protein complexes between a TGF-beta binding protein (sclerostin) and either of the bone morphogenetic protein (BMP; e.g., Schmitt et al., 1999 *J., Orthopaed. Res.* 17:269) antagonist proteins chordin (e.g., SEQ ID NOS: 19–20) and noggin (e.g., SEQ ID NOS:17–18), using surface plasmon resonance (e.g., Iemura et al., 1998 *Proc. Nat. Acad. Sci. USA* 95:9337). Chordin (e.g., Reddi et al. 2001 *Arthritis Research* 3:1; Oelgeschlager et al., 2000 Nature 405:757), cystine knot proteins such as noggin (e.g., Groppe et al., 2002 *Nature* 420:636), and the distinct DAN family of proteins (including DAN, Cerberus and Gremlin; e.g., Hsu et al., 1998 *Mol. Cell* 1:673) represent three general classifications of secreted BMP antagonist proteins that act extracellularly (e.g., Balemans et al., 2002 *Dev. Biol.* 250:231). Amino acid sequence alignment of human sclerostin (Beer) with Cerberus, DAN and Gremlin showed that despite a highly similar cysteine scaffold among the four proteins, sclerostin otherwise exhibited little homology with the DAN family members (FIG. 1; see also U.S. Pat. No. 6,395,511).

Surface Plasmon Resonance (Biacore) Analysis of the Sclerostin-BMP Interactions. Recombinant BMP proteins (R&D Systems, Inc., Minneapolis, Minn.) were hydrated to a concentration of 100 μg/ml in PBS (pH7.3) with 1 mg/ml RIA grade BSA (Sigma) and 1 mg/ml carboxyl-methyl dextran (Fluka). The running buffer for Biacore analysis was HBS-EP CMD (10 mM HEPES, 150 mM NaCl, 3 mM EDTA, 0.005% polysorbate 20, and 1 mg/ml carboxyl-methyl dextran). For kinetic analysis, CM5 sensor chips (Biacore) were made with 200 and 400 response units of purified human sclerostin-FLAG® fusion protein ("FLAG®-Beer", prepared as described in U.S. Pat. No. 6,395,511), as recommended by the chip manufacturer. BMP proteins were diluted in running buffer and injected over the sensor chip using the Biacore 3000 instrumentation. The data was processed using the Bia-evaluation software (Biacore) by first correcting for background binding in a non-functionalized flow cell and analyzing the resulting binding curves for on/off rates.

For competition experiments, the BMPs were mixed with BMP binding antibodies, BMP antagonist proteins (DAN, Noggin, Chordin, or Twisted gastrulation), or BMP receptor Fc-fusion proteins (all recombinant proteins except sclerostin from R&D systems), or with buffer only, prior to injection over the sensor chip. These mixtures were then injected over sclerostin (200 RU)-functionalized sensor chips. Using the Bia-evaluation software, the resulting surface plasmon resonance curves were compared with those generated by BMPs injected without the competitive proteins and with BMPs injected with irrelevant control proteins.

Sclerostin-Noggin and Sclerostin-Chordin Interactions. The running buffer for Biacore analysis was HBS-EP CMD (10 mM HEPES, 150 mM NaCl, 3 mM EDTA, 0.005% polysorbate 20, and 1 mg/ml carboxyl-methyl dextran). For kinetic analysis, CM5 sensor chips (Biacore) were made with 200 and 400 response units of purified human sclerostin-Flag, as recommended by the chip manufacturer. Noggin-FC fusion protein and chordin were diluted into running buffer and injected over the scierostin chip using the Biacore instrumentation. The data was processed using the Bia-evaluation software by first correcting for background binding in a non-functionalized flow cell and analyzing the resulting binding curves for on/off rates.

A surface plasmon resonance assay to examine sclerostin binding to noggin was performed by binding a noggin-Fc fusion protein to a CM5 Biacore chip that was functionalized with an anti-human Fc antibody. Binding of sclerostin to noggin in this format had similar kinetics to those seen when Noggin was bound to the CM5 Biacore chip functionalized with sclerostin.

Screening for inhibitors of the sclerostin-noggin and the sclerostin-chordin interactions using surface plasmon resonance (Biacore™). The running buffer for Biacore™ analysis was HBS-EP CMD (10 mM HEPES, 150 mM NaCl, 3 mM EDTA, 0.005% polysorbate 20, and 1 mg/ml carboxyl-methyl dextran). For kinetic analysis, CM5 sensor chips (Biacore) were made with 200 and 400 response units of purified human sclerostin-FLAG®, as recommended by the manufacturer. The Biacore command "coinject" was used to inject the saturating amounts of a first sclerostin interacting protein (BMP, noggin, chordin, or anti Sclerostin antibody) before injection of a second candidate interacting protein. To determine if one interacting protein was competitive with another, the binding curves of the protein injected second (obtained by subtracting the binding of the first protein from the combined binding curve of both proteins) were compared with the binding curve of that second protein when injected alone, following a running buffer injection. If the binding curves were similar the proteins were not competitively binding to the chip-immobilized scierostin polypeptide. If the binding curve of the second protein was greatly reduced after binding of the first protein to the chip, the proteins were regarded as competitive.

Immunoprecipitation Anti-FLAG® M2 agarose beads (Sigma, sT. Louis, Mo.) were washed three times with IP buffer (20 mM Tris, pH 7.6, 150 mM NaCl, 1 mM EDTA, 1% Triton-X 100, 1.4 mM β-mercaptoethanol, 10% glycerol) before incubation for 1 hour in the presence or absence of 4 μg of sclerostin-FLAG. Unbound sclerostin-FLAG was removed by washing with IP buffer. The beads and tubes were blocked to prevent non-specific binding by a 30-minute incubation with 5% BSA in PBS. Noggin Fc fusion protein was rehydrated according to the manufacturer's instruction, diluted into IP buffer, and centrifuged in a 4° C. microfuge for 10 minutes to remove aggregated protein. The noggin solutions were added to the beads with and without sclerostin-FLAG and incubated for 2 hours to overnight at 4° C. The immunoprecipitates were washed 5 times with IP buffer prior to the addition of SDS PAGE loading buffer. The samples were analyzed on a 10–20% gradient Tris-glycine SDS PAGE gel (Novex), transferred to nitrocellulose, and the western blots were developed with anti-Human-Fc antibodies.

Figure 6:
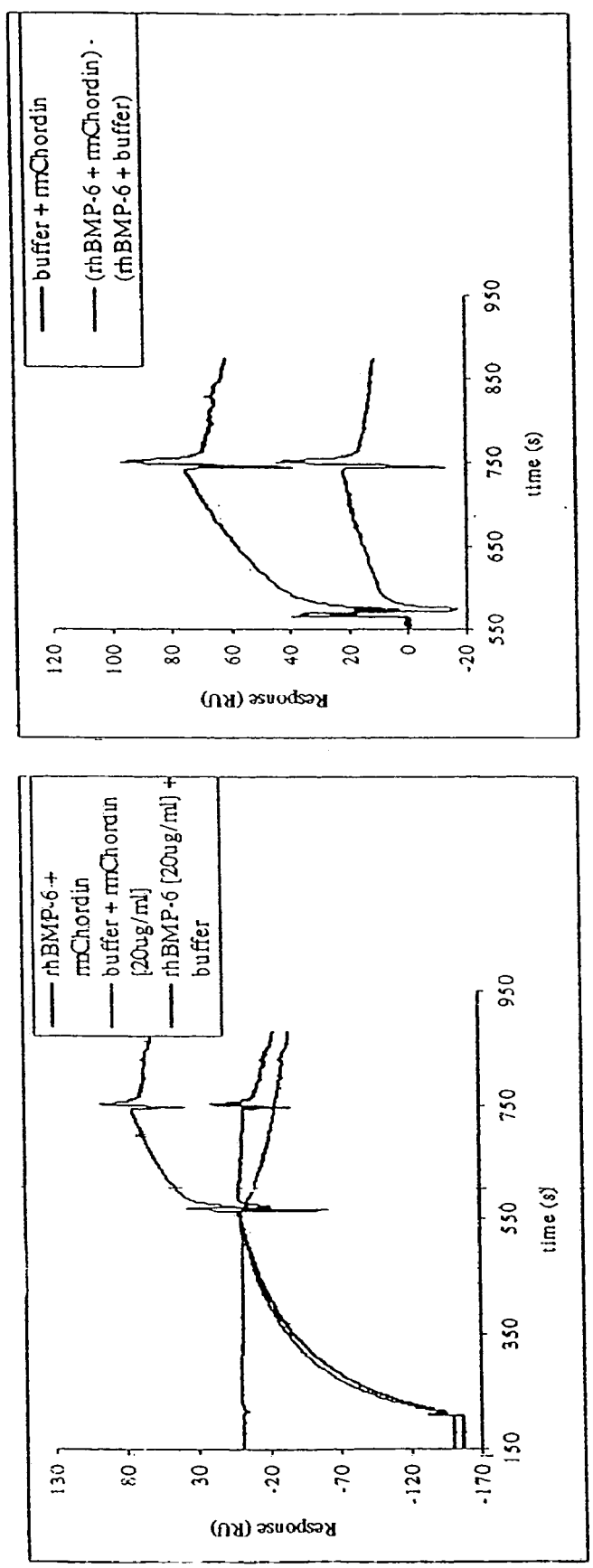
FIG. 6 shows human BMP-6 binding to human sclerostin and to rat sclerostin.
Figure 7:
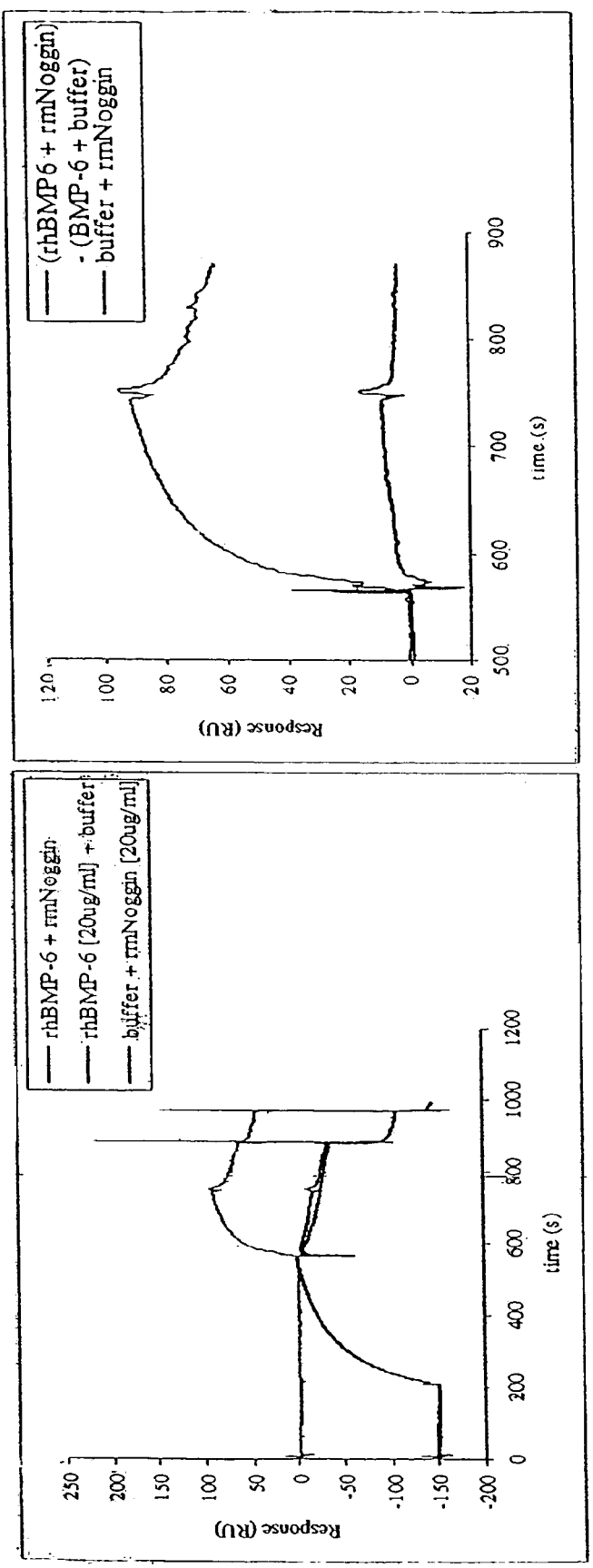
FIG. 7 shows effects of anti-BMP-6 antibodies on binding of BMP-6 to sclerostin.
Figure 8:
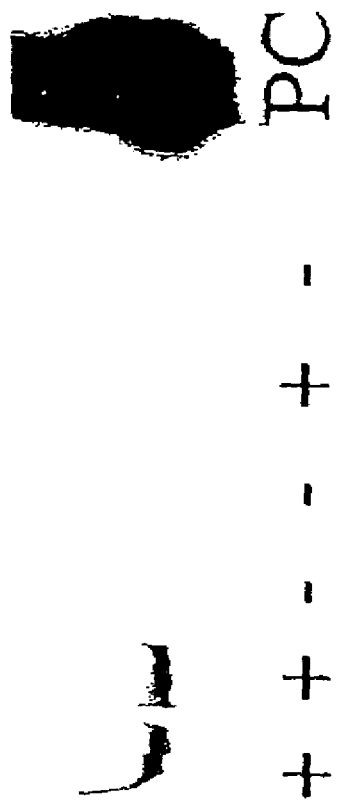
FIG. 8 shows screening of anti-sclerostin antibodies for inhibition of the BMP-6 binding interaction with sclerostin.

Results Using surface plasmon resonance (SPR) with immobilized sclerostin polypeptide, binding to sclerostin of BMP-2, BMP-4, BMP-5, BMP-6 and BMP-7 was detected with each binding interaction having a binding constant ($K_D$) in the low nanomolar range (<10–15 nM), in agreement with BMP binding interactions with sclerostin ("Beer") as previously determined (e.g., U.S. Pat. No. 6,395, 511). FIG. 6 shows SPR demonstration of human BMP-6 binding to chip-immobilized human sclerostin-FLAG® fusion protein, and to chip-immobilized poly-histidine-tagged rat sclerostin. In FIG. 7, the relative abilities of several monoclonal and polyclonal anti-BMP-6 antibodies to block binding of BMP-6 to chip-immobilized sclerostin were compared using SPR. The SPR assay for BMP-6 binding to immobilized sclerostin was used to screen for anti-sclerostin antibodies that were capable of blocking BMP-6 binding to sclerostin. A candidate antibody was first injected into the SPR instrument under conditions and for a time sufficient to permit binding to the chip-immobilized sclerostin. BMP-6 was subsequently injected and its ability to bind to sclerostin was assessed, as shown in FIG. 8.

Figure 9:
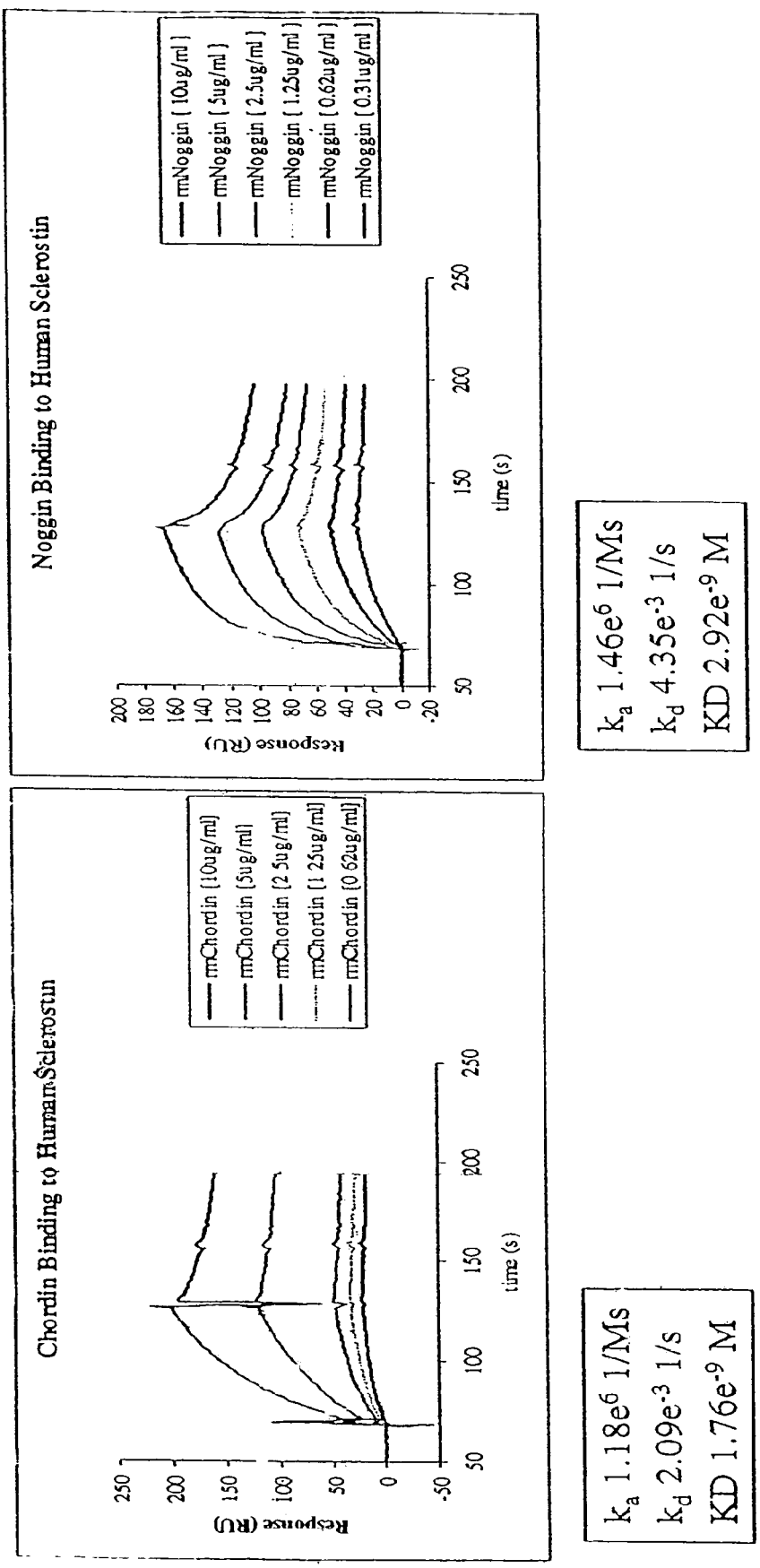
FIG. 9 shows inhibition by a polyclonal anti-sclerostin antibody of sclerostin binding by either Noggin or Chordin.

When the SPR assay was performed using chip-immobilized recombinant human sclerostin (Beer) and injections of graded concentrations of recombinant murine chordin or recombinant murine noggin, each of the BMP antagonist proteins (chordin and noggin) was observed to bind to sclerostin, as shown in FIG. 2. The $K_D$ for chordin-sclerostin binding was 1.76 nM (FIG. 2A); the $K_D$ for noggin-sclerostin binding was 2.92 nM (FIG. 2B). Binding to sclerostin by either noggin (FIG. 9A) or chordin (FIG. 9B) was inhibited in the SPR assay by first injecting a polyclonal anti-sclerostin antibody into the SPR instrument under conditions and for a time sufficient to permit binding to the chip-immobilized sclerostin.

Confirmation of noggin binding to sclerostin by an independent methodology was achieved by immunoprecipitation with anti-FLAG® beads that were pre-loaded with FLAG®-tagged sclerostin, washed, and then exposed to noggin-Fc fusion protein. As shown in FIG. 3, the noggin fusion protein was detectable by western immunoblot analysis using anti-Fc in precipitated beads that were pre-loaded with FLAG®-sclerostin, but noggin was not detected in precipitated beads that were sham-preloaded with buffer only.

Figure 4:
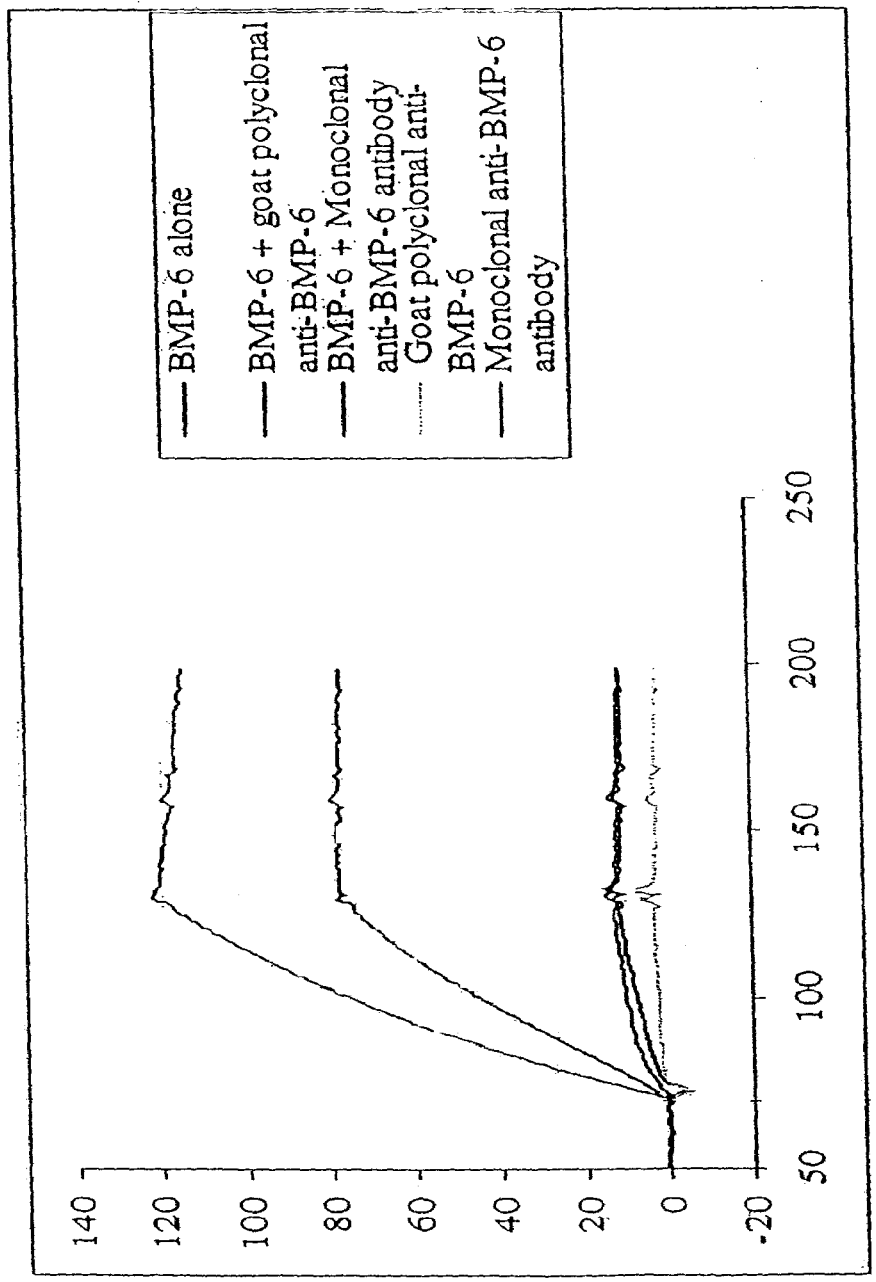
FIG. 4 shows competitive binding to sclerostin by BMP-6 and Noggin.
Figure 5:
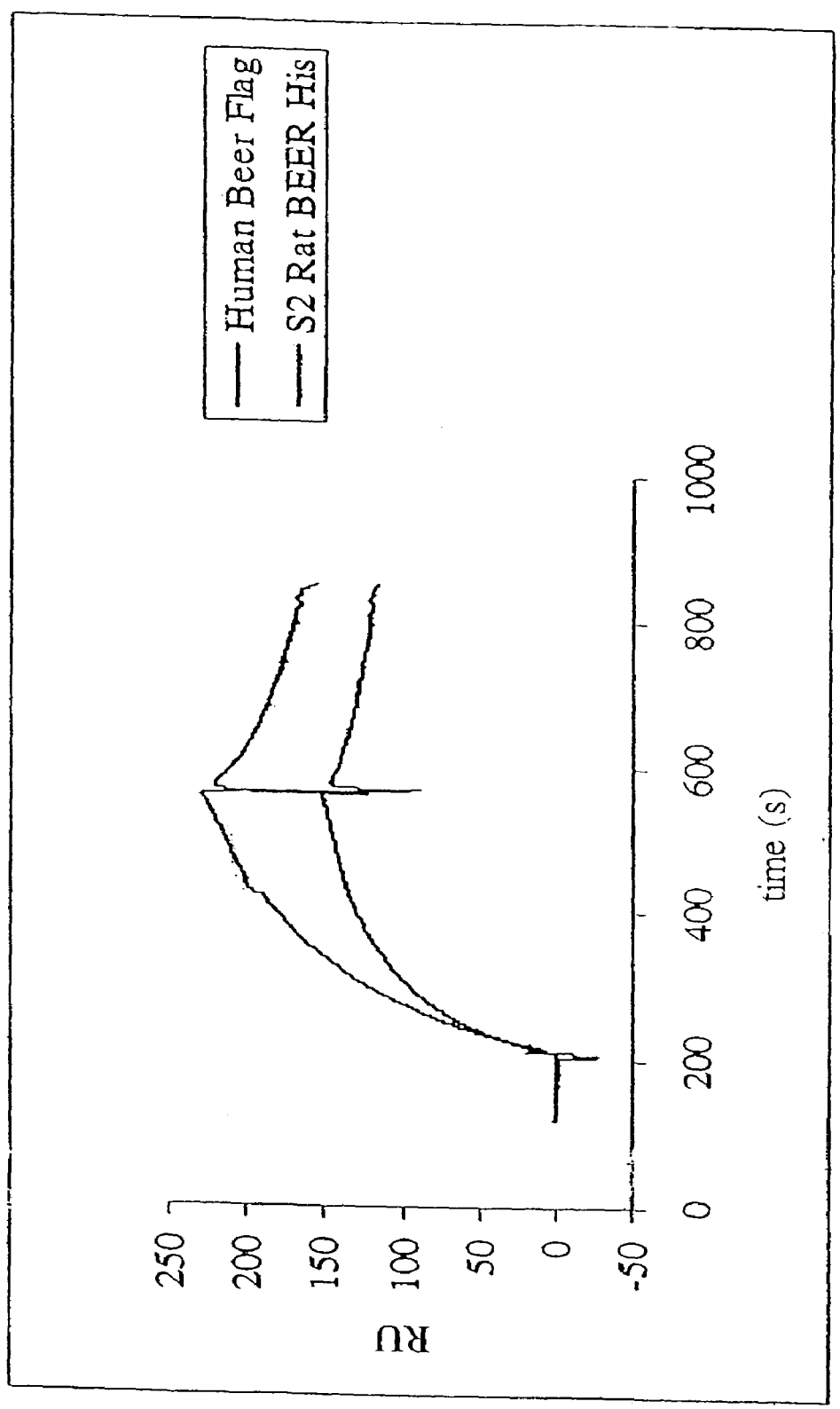
FIG. 5 shows competitive binding to sclerostin by BMP-6 and Chordin.

To determine whether the BMP antagonists noggin and chordin compete with BMP for binding to sclerostin, SPR assays using chip-immobilized sclerostin were performed with BMP-6 and BMP antagonists being exposed to sclerostin sequentially (FIG. 4A) or following a pre-mixing step (FIG. 4B). As shown in FIG. 4A, saturation of immobilized sclerostin with fluid phase BMP-6 prior to injection of noggin prevented noggin binding to sclerostin, suggesting competitive binding of BMP-6 and noggin to sclerostin. FIG. 4B shows that noggin alone bound to chip-immobilized sclerostin, while preincubation of noggin with BMP-6 prior to injection resulted in little detectable binding of either protein to sclerostin. Similar results were obtained by a comparison of the relative binding to sclerostin of chordin alone or sequentially following BMP-6 injection, as shown in FIG. 5A where prior injection of saturating amounts of BMP-6 precluded binding to sclerostin of subsequently injected chordin. FIG. 5B shows the results of a pre-mixing experiment. Immunoprecipitation analysis with bead-immobilized sclerostin of the recombinant murine chordin that was used, as obtained from the supplier (R&D Systems), indicated that a range of chordin-derived polypeptide degradation products, but apparently not the intact, full-length chordin polypeptide (approximately 100 kDa), could be detected (by western immunoblot using anti-chordin antibodies) as recoverable, specifically bound sclerostin ligands. Among the recovered chordin-derived polypeptides was a species that migrated in denaturing gel electrophoresis with a mass of approximately 25 kDa, as well as a range of smaller and larger polypeptides. A similar immunoprecipitation analysis to characterize noggin polypeptides that specifically bound to bead-immobilized sclerostin indicated that non-degraded (e.g., full length) noggin could be recovered as a sclerostin ligand.

In a cell-based assay of BMP-6 activity, as measured by determining inducible alkaline phosphatase activity in C3H10T or C3H10T1/2 cells (e.g., Ahrens et al., 1993 *DNA Cell Biol.* 12(10):871), chordin was able to block induction of the phosphatase by BMP-6. Separately, noggin was detected in immunoprecipitates prepared by reacting an anti-sclerostin antibody with lysates from a sclerostin-over-expressing osteosarcoma cell line.

Example 2

Mesenchymal Cell Assays

A small population of pluripotent mesenchymal/stromal cells, called inducible osteoprogenitor cells, can be induced to differentiate into osteoblastic cells (Pittenger, MF et al., Science, 284: 143 (1999)). These inducible osteoprogenitor cells develop and express certain phenotypic markers in a defined, sequential manner (Pockwinse, S et al., 1992 J Cell Biochem 49:310; Lian, JB et al. 1999 in *Primer on the Metabolic Bone Diseases and Disorders of Mineral Metabolism*, $4^{th}$ edition, M J Favus (ed), Lippincott, Philadelphia, pg. 14.). Osteoprogenitor cells express type I collagen whereas committed pre-osteoblasts and osteoblasts express many of the phenotypic markers that are typically identified with a cell of the osteoblast lineage. These markers include type I collagen, alkaline phosphatase, parathyroid hormone receptor (PTHr) and osteopontin. In the terminal stage of osteoblast differentiation, osteocytes are surrounded by deposits of mineral as well as matrix proteins such as CD44 and osteocalcin. Therefore, the development, growth and differentiation of osteoblastic precursor cells into mature osteoblasts occur in a defined, time-dependent manner (Pockwinse, S et al., 1992 J Cell Biochem 49:310).

Primary human mesenchymal cells, primary human osteoblasts and corresponding media are available from Biowhittaker (Walkersville, Md.). Mouse mesenchymal C3H10T1/2 cells are available from American Type Culture Collection (Manassas, Va.) (ATCC Deposit No. CCL-226). As immature osteoblasts differentiate and become capable of mineralization, they express markers associated with the osteoblast phenotype (type I collagen and parathyroid hormone receptor (PTHr)). These markers are used to ascertain whether differentiation has occurred. Human mesenchymal cells and primary human osteoblasts are plated in regular growth media containing 2% FCS at a density of 10,000 cells/cm². Test reagents are added singly or in combination on the following day. Cultures are continued for 24 to 120 hrs after which the cells are harvested for RNA isolation. Untreated hMSC cells will strongly express type I collagen, with negligible levels of PTHr and SOST. Such results indicate that untreated hMSC cells are in an early stage of osteoblast lineage, but are committed to osteoblastogenesis. Treatment of these cells with DEX, bone morphogenetic proteins, IGF-1 (IGF-1 at 50 ng/ml) or long-term culture in osteoblast-inducing media will advance the stage of differentiation and induce PTHr expression.

To determine the effect of an agent identified herein on human mesenchymal cells, hMSC cells are plated in 96-well tissue culture dishes at a density of 10,000 cells/cm² in Osteoblast-Inducing medium. The agent is prepared in an appropriate vehicle, and an equal volume of Sf9 conditioned media (Control) is added to cultures of hMSC cells at various times after plating (1 day, 8 days, 15 days, or 21 days). The effects of the agent on osteoblastic differentiation are assessed by measuring alkaline phosphatase activity (ALP, determined in cell layers using DEM buffer (Pierce) containing 0.5% NP-40 and 10 mM p-nitrophenylphosphate), synthesis of collagen type I (Prolagen C ELISA), and calcium deposition for mineralization (calorimetric assay of acid lysates of cell layers, Sigma).

To determine the effects of an agent identified herein on mouse mesenchymal C3H10T1/2 cells, C3H10T1/2 cells (ATCC Deposit No. CCL-226) are plated in 96-well dishes at a density of 25,000 cells per well in complete growth medium (DMEM with high glucose and glutamine supplemented with 10% FCS, 1% penicillin/streptomycin, 0.1 mM non-essential amino acids, 1 mM sodium pyruvate, 55 µM β-mercaptoethanol, and 20 mM HEPES, pH 7.3). C3H10T1/2 cells can be used in a short-term (72 hr) assay to determine the effects of an agent on BMP-induced ALP activity. The agent is prepared in an appropriate vehicle, and an equal volume of Sf9 conditioned media (control) is pre-incubated with 500 ng/ml BMP-6 for 1 hr prior to addition to cells. For comparison, similar incubations are carried out with anti-BMP-6 antibody and noggin. Cells are harvested 72 hrs later for determination of ALP activity.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. An isolated complex comprising a TGF-beta binding protein and a BMP antagonist protein in specific association, wherein: (i) the TGF-beta binding protein comprises a sclerostin polypeptide that is capable of specifically binding a first TGF-beta superfamily member polypeptide that is selected from the group consisting of a BMP-5 polypeptide and a BMP-6 polypeptide, and (ii) the BMP antagonist protein is selected from the group consisting of a Chordin polypeptide and a Noggin polypeptide, said BMP antagonist protein being capable of specifically binding at least one second TGF-beta superfamily member polypeptide that is selected from the group consisting of a BMP-2 polypeptide, a BMP-4 polypeptide and a BMP-7 polypeptide, and wherein the complex is incapable of binding to the first TGF-beta superfamily member polypeptide.

2. An isolated complex comprising a first and a second TGF-beta binding protein in specific association, wherein; (a) the first TGF-beta binding protein is capable of binding a first TGF-beta superfamily member that is a first cognate ligand; and (b) the second TGF-beta binding protein is capable of binding a second TGF-beta superfamily member that is a second cognate ligand; wherein the complex is incapable of binding to either of the first and second cognate ligands, and wherein the first TGF-beta binding protein comprises a sclerostin polypeptide and the first cognate ligand is at least one polypeptide selected from the group consisting of BMP-2, BMP-4, BMP-5, BMP-6 and BMP-7, and wherein the second TGF-beta binding protein comprises a chordin polypeptide and the second cognate ligand is a polypeptide selected from the group consisting of BMP 2, BMP-4 and BMP-7.

3. An isolated complex comprising a first and a second TGF-beta binding protein in specific association, wherein; (a) the first TGF-beta binding protein is capable of binding a first TGF-beta superfamily member that is a first cognate ligand; and (b) the second TGF-beta binding protein is capable of binding a second TGF-beta superfamily member that is a second cognate ligand; wherein the complex is incapable of binding to either of the first and second cognate ligands, and wherein the first TGF-beta binding protein comprises a sclerostin polypeptide and the first cognate ligand is a polypeptide selected from the group consisting of BMP-5 and BMP-6, and wherein the second TGF-beta binding protein comprises a noggin polypeptide and the second cognate ligand is a polypeptide selected from the group consisting of BMP-2, BMP-4, BMP-7, and GDF-5.

* * * * *

SEQUENCE LISTING

<160> NUMBER OF SEQ ID NOS: 20

<210> SEQ ID NO 1
<211> LENGTH: 2301
<212> TYPE: DNA
<213> ORGANISM: Homo sapiens

<400> SEQUENCE: 1

```
agagcctgtg ctactggaag gtggcgtgcc ctcctctggc tggtaccatg cagctcccac      60
tggccctgtg tctcgtctgc ctgctggtac acacagcctt ccgtgtagtg gagggccagg     120
ggtggcaggc gttcaagaat gatgccacgg aaatcatccc cgagctcgga gagtaccccg     180
agcctccacc ggagctggag aacaacaaga ccatgaaccg ggcggagaac ggagggcggc     240
ctccccacca cccctttgag accaaagacg tgtccgagta cagctgccgc gagctgcact     300
tcacccgcta cgtgaccgat gggccgtgcc gcagcgccaa gccggtcacc gagctggtgt     360
gctccggcca gtgcggcccg gcgcgcctgc tgcccaacgc catcggccgc ggcaagtggt     420
ggcgacctag tgggcccgac ttccgctgca tccccgaccg ctaccgcgcg cagcgcgtgc     480
agctgctgtg tcccggtggt gaggcgccgc gcgcgcgcaa ggtgcgcctg gtggcctcgt     540
gcaagtgcaa gcgcctcacc cgcttccaca accagtcgga gctcaaggac ttcgggaccg     600
aggccgctcg gccgcagaag ggccggaagc cgcggccccg cgcccggagc gccaaagcca     660
accaggccga gctggagaac gcctactaga gcccgcccgc gccccctcccc accggcgggc     720 gccccggccc tgaacccgcg ccccacattt ctgtcctctg cgcgtggttt gattgtttat     780
atttcattgt aaatgcctgc aacccagggc aggggggctga gaccttccag gccctgagga     840
atcccgggcg ccggcaaggc ccccctcagc ccgccagctg aggggtccca cggggcaggg     900
gagggaattg agagtcacag acactgagcc acgcagcccc gcctctgggg ccgcctacct     960
ttgctggtcc cacttcagag gaggcagaaa tggaagcatt ttcaccgccc tggggttttta    1020 agggagcggt gtgggagtgg gaaagtccag ggactggtta agaaagttgg ataagattcc    1080
cccttgcacc tcgctgccca tcagaaagcc tgaggcgtgc ccagagcaca agactggggg    1140
caactgtaga tgtggtttct agtcctggct ctgccactaa cttgctgtgt aaccttgaac    1200
tacacaattc tccttcggga cctcaatttc cactttgtaa aatgagggtg gaggtgggaa    1260
taggatctcg aggagactat tggcatatga ttccaaggac tccagtgcct tttgaatggg    1320
cagaggtgag agagagagag agaaagagag agaatgaatg cagttgcatt gattcagtgc    1380
caaggtcact tccagaattc agagttgtga tgctctcttc tgacagccaa agatgaaaaa    1440
caaacagaaa aaaaaagta aagagtctat ttatggctga catatttacg gctgacaaac    1500
tcctggaaga agctatgctg cttcccagcc tggcttcccc ggatgtttgg ctacctccac    1560
ccctccatct caaagaaata acatcatcca ttggggtaga aaggagagg gtccgagggt    1620 ggtgggaggg atagaaatca catccgcccc aacttcccaa agagcagcat ccctcccccg    1680
```

-continued

```
acccatagcc atgttttaaa gtcaccttcc gaagagaagt gaaaggttca aggacactgg   1740
ccttgcaggc ccgagggagc agccatcaca aactcacaga ccagcacatc ccttttgaga   1800
<br>

caccgccttc tgcccaccac tcacggacac atttctgcct agaaaacagc ttcttactgc   1860
tcttacatgt gatggcatat cttacactaa aagaatatta ttgggggaaa aactacaagt   1920
gctgtacata tgctgagaaa ctgcagagca taatagctgc cacccaaaaa tctttttgaa   1980
aatcatttcc agacaacctc ttactttctg tgtagttttt aattgttaaa aaaaaaaagt   2040
tttaaacaga agcacatgac atatgaaagc ctgcaggact ggtcgttttt ttggcaattc   2100
ttccacgtgg gacttgtcca caagaatgaa agtagtggtt tttaaagagt taagttacat   2160
atttattttc tcacttaagt tatttatgca aaagtttttc ttgtagagaa tgacaatgtt   2220
aatattgctt tatgaattaa cagtctgttc ttccagagtc cagagacatt gttaataaag   2280
acaatgaatc atgaccgaaa g                                              2301
```

<210> SEQ ID NO 2
<211> LENGTH: 213
<212> TYPE: PRT
<213> ORGANISM: Homo sapiens

<400> SEQUENCE: 2

```
Met Gln Leu Pro Leu Ala Leu Cys Leu Val Cys Leu Leu Val His Thr
 1               5                  10                  15

Ala Phe Arg Val Val Glu Gly Gln Gly Trp Gln Ala Phe Lys Asn Asp
            20                  25                  30

Ala Thr Glu Ile Ile Pro Glu Leu Gly Glu Tyr Pro Glu Pro Pro Pro
        35                  40                  45

Glu Leu Glu Asn Asn Lys Thr Met Asn Arg Ala Glu Asn Gly Gly Arg
    50                  55                  60

Pro Pro His His Pro Phe Glu Thr Lys Asp Val Ser Glu Tyr Ser Cys
65                  70                  75                  80

Arg Glu Leu His Phe Thr Arg Tyr Val Thr Asp Gly Pro Cys Arg Ser
                85                  90                  95

Ala Lys Pro Val Thr Glu Leu Val Cys Ser Gly Gln Cys Gly Pro Ala
            100                 105                 110

Arg Leu Leu Pro Asn Ala Ile Gly Arg Gly Lys Trp Trp Arg Pro Ser
        115                 120                 125

Gly Pro Asp Phe Arg Cys Ile Pro Asp Arg Tyr Arg Ala Gln Arg Val
    130                 135                 140

Gln Leu Leu Cys Pro Gly Gly Glu Ala Pro Arg Ala Arg Lys Val Arg
145                 150                 155                 160

Leu Val Ala Ser Cys Lys Cys Lys Arg Leu Thr Arg Phe His Asn Gln
                165                 170                 175

Ser Glu Leu Lys Asp Phe Gly Thr Glu Ala Ala Arg Pro Gln Lys Gly
            180                 185                 190

Arg Lys Pro Arg Pro Arg Ala Arg Ser Ala Lys Ala Asn Gln Ala Glu
        195                 200                 205

Leu Glu Asn Ala Tyr
    210
```

<210> SEQ ID NO 3
<211> LENGTH: 2301
<212> TYPE: DNA
<213> ORGANISM: Homo sapiens -continued

<400> SEQUENCE: 3

```
agagcctgtg ctactggaag gtggcgtgcc ctcctctggc tggtaccatg cagctcccac      60
tggccctgtg tctcgtctgc ctgctggtac acacagcctt ccgtgtagtg gagggctagg     120
ggtggcaggc gttcaagaat gatgccacgg aaatcatccc cgagctcgga gagtaccccg     180
agcctccacc ggagctggag aacaacaaga ccatgaaccg ggcggagaac ggagggcggc     240
ctccccacca ccccttttgag accaaagacg tgtccgagta cagctgccgc gagctgcact    300
tcacccgcta cgtgaccgat gggccgtgcc gcagcgccaa gccggtcacc gagctggtgt    360
gctccggcca gtgcggcccg cgcgcgcctg ctgcccaacgc atcggccgc ggcaagtggt     420
ggcgacctag tgggcccgac ttccgctgca tccccgaccg ctaccgcgcg cagcgcgtgc     480
agctgctgtg tccggtggt gaggcgccgc gcgcgcgcaa ggtgcgcctg gtggcctcgt      540
gcaagtgcaa gcgcctcacc cgcttccaca accagtcgga gctcaaggac ttcgggaccg     600
aggccgctcg gccgcagaag ggccggaagc cgcggccccg cgcccggagc gccaaagcca    660
accaggccga gctggagaac gcctactaga gcccgcccgc gcccctcccc accggcgggc    720
gccccggccc tgaacccgcg ccccacattt ctgtcctctg cgcgtggttt gattgtttat    780
atttcattgt aaatgcctgc aacccagggc agggggctga gccttccag gccctgagga    840
atcccgggcg ccgcaaggc cccctcagc ccgccagctg aggggtccca cggggcaggg      900
gagggaattg agagtcacag acactgagcc acgcagcccc gcctctgggg ccgcctacct    960
ttgctggtcc cacttcagag gaggcagaaa tggaagcatt ttcaccgccc tggggtttta  1020
agggagcggt gtgggagtgg gaaagtccag ggactggtta agaaagttgg ataagattcc   1080
cccttgcacc tcgctgccca tcagaaagcc tgaggcgtgc ccagagcaca agactggggg  1140
caactgtaga tgtggtttct agtcctggct ctgccactaa cttgctgtgt aaccttgaac   1200
tacacaattc tccttcggga cctcaatttc cactttgtaa aatgagggtg gaggtgggaa   1260
taggatctcg aggagactat tggcatatga ttccaaggac tccagtgcct tttgaatggg   1320
cagaggtgag agagagagag agaaagagag agaatgaatg cagttgcatt gattcagtgc   1380
caaggtcact tccagaattc agagttgtga tgctctcttc tgacagccaa agatgaaaaa   1440
caaacagaaa aaaaaagta aagagtctat ttatggctga catatttacg gctgacaaac    1500
tcctggaaga agctatgctg cttcccagcc tggcttcccc ggatgtttgg ctacctccac    1560
ccctccatct caaagaaata acatcatcca ttgggtaga aaggagagg gtccgagggt    1620
ggtgggaggg atagaaatca catccgcccc aacttcccaa agagcagcat ccctcccccg   1680
acccatagcc atgttttaaa gtcaccttcc gaagagaagt gaaaggttca aggacactgg   1740
ccttgcaggc ccgagggagc agccatcaca aactcacaga ccagcacatc ccttttgaga   1800
caccgccttc tgcccaccac tcacggacac atttctgcct agaaaacagc ttcttactgc    1860
tcttacatgt gatggcatat cttacactaa agaatatta ttgggggaaa aactacaagt    1920
gctgtacata tgctgagaaa ctgcagagca taatagctgc cacccaaaaa tctttttgaa   1980
aatcatttcc agacaacctc ttactttctg tgtagttttt aattgttaaa aaaaaaagt   2040
tttaaacaga agcacatgac atatgaaagc ctgcaggact ggtcgttttt ttggcaattc   2100
ttccacgtgg gacttgtcca caagaatgaa agtagtggtt tttaaagagt taagttacat   2160
atttattttc tcacttaagt tatttatgca aaagttttc ttgtagagaa tgacaatgtt    2220
aatattgctt tatgaattaa cagtctgttc ttccagagtc cagagacatt gttaataaag    2280
acaatgaatc atgaccgaaa g                                              2301
```

<210> SEQ ID NO 4
<211> LENGTH: 23
<212> TYPE: PRT
<213> ORGANISM: Homo sapiens

<400> SEQUENCE: 4

Met Gln Leu Pro Leu Ala Leu Cys Leu Val Cys Leu Leu Val His Thr
1               5                   10                  15

Ala Phe Arg Val Val Glu Gly
            20

<210> SEQ ID NO 5
<211> LENGTH: 2301
<212> TYPE: DNA
<213> ORGANISM: Homo sapiens

<400> SEQUENCE: 5
agagcctgtg ctactggaag gtggcgtgcc ctcctctggc tggtaccatg cagctcccac      60
tggccctgtg tctcatctgc ctgctggtac acacagcctt ccgtgtagtg gagggccagg     120
ggtggcaggc gttcaagaat gatgccacgg aaatcatccg cgagctcgga gagtaccccg     180
agcctccacc ggagctggag aacaacaaga ccatgaaccg gcggagaaac ggagggcggc     240
ctccccacca cccctttgag accaaagacg tgtccgagta cagctgccgc gagctgcact     300
tcacccgcta cgtgaccgat gggcgtgcc cagcgccaa gcggtcacc gagctggtgt       360 gctccggcca gtgcggcccg cgcgcgcctg tgcccaacgc catcggccgc ggcaagtggt     420
ggcgacctag tgggcccgac ttccgctgca tccccgaccg ctaccgcgcg cagcgcgtgc     480
agctgctgtg tccccggtggt gaggcgccgc gcgcgcgcaa ggtgcgcctg gtggcctcgt     540
gcaagtgcaa gcgcctcacc cgcttccaca accagtcgga gctcaaggac ttcgggaccg     600
aggccgctcg gccgcagaag ggccggaagc cgcggcccccg cgcccggagc gccaaagcca     660
accaggccga gctggagaac gcctactaga gcccgcccgc gcccctcccc accggcgggc     720
gccccggccc tgaacccgcg ccccacattt ctgtcctctg cgcgtggttt gattgtttat     780
atttcattgt aaatgcctgc aacccagggc aggggctga gaccttccag gccctgagga      840
atcccgggcg ccggcaaggc cccctcagc ccgccagctg aggggtccca cggggcaggg      900
gagggaattg agagtcacag acactgagcc acgcagcccc gcctctgggg ccgcctacct     960
ttgctggtcc cacttcagag gaggcagaaa tggaagcatt ttcaccgccc tggggttttta    1020 agggagcggt gtgggagtgg gaaagtccag ggactggtta agaaagttgg ataagattcc    1080
cccttgcacc tcgctgccca tcagaaagcc tgaggcgtgc ccagagcaca agactggggg    1140
caactgtaga tgtggtttct agtcctggct ctgccactaa cttgctgtgt aaccttgaac    1200
tacacaattc tccttcggga cctcaatttc cactttgtaa atgagggtg gaggtgggaa    1260 taggatctcg aggagactat tggcatatga ttccaaggac tccagtgcct tttgaatggg    1320
cagaggtgag agagagagag agaaagagag agaatgaatg cagttgcatt gattcagtgc    1380
caaggtcact tccagaattc agagttgtga tgctctcttc tgacagccaa agatgaaaaa    1440
caaacagaaa aaaaaagta aagagtctat ttatggctga catatttacg gctgacaaac    1500
tcctggaaga agctatgctg cttcccagcc tggcttcccc ggatgtttgg ctacctccac    1560
ccctccatct caaagaaata acatcatcca ttggggtaga aaggagagg gtccgagggt    1620 ggtgggaggg atagaaatca catccgcccc aacttcccaa agagcagcat ccctcccccg    1680

```
acccatagcc atgttttaaa gtcaccttcc gaagagaagt gaaaggttca aggacactgg    1740
ccttgcaggc ccgagggagc agccatcaca aactcacaga ccagcacatc ccttttgaga    1800
caccgccttc tgcccaccac tcacggacac atttctgcct agaaaacagc ttcttactgc    1860
tcttacatgt gatggcatat cttacactaa agaatatta ttgggggaaa aactacaagt     1920
gctgtacata tgctgagaaa ctgcagagca taatagctgc acccaaaaa tcttttgaa      1980 aatcatttcc agacaacctc ttactttctg tgtagttttt aattgttaaa aaaaaaagt     2040 tttaaacaga agcacatgac atatgaaagc ctgcaggact ggtcgttttt ttggcaattc    2100
ttccacgtgg gacttgtcca caagaatgaa agtagtggtt tttaaagagt taagttacat    2160
atttattttc tcacttaagt tatttatgca aagttttc ttgtagagaa tgacaatgtt      2220
aatattgctt tatgaattaa cagtctgttc ttccagagtc cagagacatt gttaataaag    2280
acaatgaatc atgaccgaaa g                                              2301
```

<210> SEQ ID NO 6
<211> LENGTH: 213
<212> TYPE: PRT
<213> ORGANISM: Homo sapiens

<400> SEQUENCE: 6

```
Met Gln Leu Pro Leu Ala Leu Cys Leu Ile Cys Leu Leu Val His Thr
 1               5                  10                  15

Ala Phe Arg Val Val Glu Gly Gln Gly Trp Gln Ala Phe Lys Asn Asp
                20                  25                  30

Ala Thr Glu Ile Ile Arg Glu Leu Gly Glu Tyr Pro Glu Pro Pro Pro
             35                  40                  45

Glu Leu Glu Asn Asn Lys Thr Met Asn Arg Ala Glu Asn Gly Gly Arg
         50                  55                  60

Pro Pro His Pro Phe Glu Thr Lys Asp Val Ser Glu Tyr Ser Cys
65                  70                  75                  80

Arg Glu Leu His Phe Thr Arg Tyr Val Thr Asp Gly Pro Cys Arg Ser
                 85                  90                  95

Ala Lys Pro Val Thr Glu Leu Val Cys Ser Gly Gln Cys Gly Pro Ala
            100                 105                 110

Arg Leu Leu Pro Asn Ala Ile Gly Arg Gly Lys Trp Trp Arg Pro Ser
        115                 120                 125

Gly Pro Asp Phe Arg Cys Ile Pro Asp Arg Tyr Arg Ala Gln Arg Val
130                 135                 140

Gln Leu Leu Cys Pro Gly Gly Glu Ala Pro Arg Ala Arg Lys Val Arg
145                 150                 155                 160

Leu Val Ala Ser Cys Lys Cys Lys Arg Leu Thr Arg Phe His Asn Gln
                165                 170                 175

Ser Glu Leu Lys Asp Phe Gly Thr Glu Ala Ala Arg Pro Gln Lys Gly
            180                 185                 190

Arg Lys Pro Arg Pro Arg Ala Arg Ser Ala Lys Ala Asn Gln Ala Glu
        195                 200                 205

Leu Glu Asn Ala Tyr
        210
```

<210> SEQ ID NO 7
<211> LENGTH: 2301
<212> TYPE: DNA
<213> ORGANISM: Homo sapiens

<400> SEQUENCE: 7

-continued

```
agagcctgtg ctactggaag gtggcgtgcc ctcctctggc tggtaccatg cagctcccac      60
tggccctgtg tctcgtctgc ctgctggtac acacagcctt ccgtgtagtg gagggccagg     120
ggtggcaggc gttcaagaat gatgccacgg aaatcatccg cgagctcgga gagtaccccg     180
agcctccacc ggagctggag aacaacaaga ccatgaaccg gcggagaaac ggagggcggc     240
ctccccacca cccctttgag accaaagacg tgtccgagta cagctgccgc gagctgcact     300
tcacccgcta cgtgaccgat gggccgtgcc gcagcgccaa gccggtcacc gagctggtgt     360
gctccggcca gtgcggcccg cgcgcgcctgc tgcccaacgc catcggccgc ggcaagtggt     420
ggcgacctag tgggcccgac ttccgctgca tccccgaccg ctaccgcgcg cagcgcgtgc     480
agctgctgtg tccggtggt gaggcgccgc gcgcgcgcaa ggtgcgcctg gtggcctcgt      540
gcaagtgcaa gcgcctcacc cgcttccaca accagtcgga gctcaaggac ttcgggaccg     600
aggccgctcg gccgcagaag ggccggaagc cgcggccccg cgcccggagc gccaaagcca     660
accaggccga gctggagaac gcctactaga gcccgcccgc gccctcccc accggcgggc      720
gccccggccc tgaacccgcg ccccacattt ctgtcctctg cgcgtggttt gattgtttat     780
atttcattgt aaatgcctgc aacccagggc aggggggctga gaccttccag gccctgagga    840
atcccgggcg ccggcaaggc cccctcagc ccgccagctg aggggtccca cggggcaggg     900
gagggaattg agagtcacag acactgagcc acgcagcccc gcctctgggg ccgcctacct    960
ttgctggtcc cacttcagag gaggcagaaa tggaagcatt ttcaccgccc tggggttta     1020
agggagcggt gtgggagtgg gaaagtccag ggactggtta agaaagttgg ataagattcc    1080
cccttgcacc tcgctgccca tcagaaagcc tgaggcgtgc ccagagcaca agactggggg    1140
caactgtaga tgtggtttct agtcctggct ctgccactaa cttgctgtgt aaccttgaac    1200
tacacaattc tccttcggga cctcaatttc cactttgtaa atgagggtg gaggtgggaa     1260
taggatctcg aggagactat tggcatatga ttccaaggac tccagtgcct tttgaatggg    1320
cagaggtgag agagagagag agaaagagag agaatgaatg cagttgcatt gattcagtgc    1380
caaggtcact tccagaattc agagttgtga tgctctcttc tgacagccaa agatgaaaaa    1440
caaacagaaa aaaaaagta aagagtctat ttatggctga catatttacg gctgacaaac    1500
tcctggaaga agctatgctg cttcccagcc tggcttcccc ggatgtttgg ctacctccac    1560
ccctccatct caaagaaata acatcatcca ttgggggtaga aaaggagagg gtccgagggt    1620
ggtgggaggg atagaaatca catccgcccc aacttcccaa agagcagcat ccctcccccg    1680
acccatagcc atgtttttaaa gtcaccttcc gaagagaagt gaaaggttca aggacactgg    1740
ccttgcaggc ccgagggagc agccatcaca aactcacaga ccagcacatc ccttttgaga    1800
caccgccttc tgcccaccac tcacggacac atttctgcct agaaacagc ttcttactgc      1860
tcttacatgt gatggcatat cttacactaa aagaatatta ttggggggaaa aactacaagt   1920
gctgtacata tgctgagaaa ctgcagagca taatagctgc cacccaaaaa tcttttttgaa   1980
aatcatttcc agacaacctc ttactttctg tgtagttttt aattgttaaa aaaaaaaagt    2040
tttaaacaga agcacatgac atatgaaagc ctgcaggact ggtcgttttt ttggcaattc    2100
ttccacgtgg gacttgtcca caagaatgaa agtagtggtt tttaaagagt taagttacat    2160
atttattttc tcacttaagt tatttatgca aaagtttttc ttgtagagaa tgacaatgtt    2220
aatattgctt tatgaattaa cagtctgttc ttccagagtc cagagacatt gttaataaag    2280
acaatgaatc atgaccgaaa g                                               2301
```

<210> SEQ ID NO 8
<211> LENGTH: 213
<212> TYPE: PRT
<213> ORGANISM: Homo sapiens

<400> SEQUENCE: 8

```
Met Gln Leu Pro Leu Ala Leu Cys Leu Val Cys Leu Leu Val His Thr
 1               5                  10                  15
Ala Phe Arg Val Val Glu Gly Gln Gly Trp Gln Ala Phe Lys Asn Asp
                20                  25                  30
Ala Thr Glu Ile Ile Arg Glu Leu Gly Glu Tyr Pro Glu Pro Pro Pro
            35                  40                  45
Glu Leu Glu Asn Asn Lys Thr Met Asn Arg Ala Glu Asn Gly Gly Arg
        50                  55                  60
Pro Pro His His Pro Phe Glu Thr Lys Asp Val Ser Glu Tyr Ser Cys
65                  70                  75                  80
Arg Glu Leu His Phe Thr Arg Tyr Val Thr Asp Gly Pro Cys Arg Ser
                85                  90                  95
Ala Lys Pro Val Thr Glu Leu Val Cys Ser Gly Gln Cys Gly Pro Ala
            100                 105                 110
Arg Leu Leu Pro Asn Ala Ile Gly Arg Gly Lys Trp Trp Arg Pro Ser
        115                 120                 125
Gly Pro Asp Phe Arg Cys Ile Pro Asp Arg Tyr Arg Ala Gln Arg Val
    130                 135                 140
Gln Leu Leu Cys Pro Gly Gly Glu Ala Pro Arg Ala Arg Lys Val Arg
145                 150                 155                 160
Leu Val Ala Ser Cys Lys Cys Lys Arg Leu Thr Arg Phe His Asn Gln
                165                 170                 175
Ser Glu Leu Lys Asp Phe Gly Thr Glu Ala Ala Arg Pro Gln Lys Gly
            180                 185                 190
Arg Lys Pro Arg Pro Arg Ala Arg Ser Ala Lys Ala Asn Gln Ala Glu
        195                 200                 205
Leu Glu Asn Ala Tyr
    210
```

<210> SEQ ID NO 9
<211> LENGTH: 642
<212> TYPE: DNA
<213> ORGANISM: Cercopithecus pygerythrus

<400> SEQUENCE: 9

```
atgcagctcc cactggccct gtgtcttgtc tgcctgctgg tacacgcagc cttccgtgta    60
gtggagggcc aggggtggca ggccttcaag aatgatgcca ggaaatcat ccccgagctc    120
ggagagtacc ccgagcctcc accggagctg gagaacaaca agaccatgaa ccgggcggag    180
aatggagggc ggcctcccca ccacccctt gagaccaaag acgtgtccga gtacagctgc    240
cgagagctgc acttcacccg ctacgtgacc gatgggccgt gccgcagcgc caagccagtc    300
accgagttgg tgtgctccgg ccagtgcggc cggcacgcc tgctgcccaa cgccatcggc    360
cgcggcaagt ggtggcgccc gagtgggccc gacttccgct gcatccccga ccgctaccgc    420
gcgcagcgtg tgcagctgct gtgtcccggt ggtgccgcgc cgcgcgcgcg caaggtgcgc    480
ctggtggcct cgtgcaagtg caagcgcctc acccgcttcc acaaccagtc ggagctcaag    540
gacttcggtc ccgaggccgc tcggccgcag aagggccgga agccgcggcc ccgcgcccgg    600
ggggccaaag ccaatcaggc cgagctggag aacgcctact ag                       642
```

<210> SEQ ID NO 10
<211> LENGTH: 213
<212> TYPE: PRT
<213> ORGANISM: Cercopithecus pygerythrus

<400> SEQUENCE: 10

```
Met Gln Leu Pro Leu Ala Leu Cys Leu Val Cys Leu Leu Val His Ala
  1               5                  10                  15

Ala Phe Arg Val Val Glu Gly Gln Gly Trp Gln Ala Phe Lys Asn Asp
             20                  25                  30

Ala Thr Glu Ile Ile Pro Glu Leu Gly Glu Tyr Pro Glu Pro Pro Pro
         35                  40                  45

Glu Leu Glu Asn Asn Lys Thr Met Asn Arg Ala Glu Asn Gly Gly Arg
     50                  55                  60

Pro Pro His His Pro Phe Glu Thr Lys Asp Val Ser Glu Tyr Ser Cys
 65                  70                  75                  80

Arg Glu Leu His Phe Thr Arg Tyr Val Thr Asp Gly Pro Cys Arg Ser
                 85                  90                  95

Ala Lys Pro Val Thr Glu Leu Val Cys Ser Gly Gln Cys Gly Pro Ala
            100                 105                 110

Arg Leu Leu Pro Asn Ala Ile Gly Arg Gly Lys Trp Trp Arg Pro Ser
        115                 120                 125

Gly Pro Asp Phe Arg Cys Ile Pro Asp Arg Tyr Arg Ala Gln Arg Val
    130                 135                 140

Gln Leu Leu Cys Pro Gly Gly Ala Ala Pro Arg Ala Arg Lys Val Arg
145                 150                 155                 160

Leu Val Ala Ser Cys Lys Cys Lys Arg Leu Thr Arg Phe His Asn Gln
                165                 170                 175

Ser Glu Leu Lys Asp Phe Gly Pro Glu Ala Ala Arg Pro Gln Lys Gly
            180                 185                 190

Arg Lys Pro Arg Pro Arg Ala Arg Gly Ala Lys Ala Asn Gln Ala Glu
        195                 200                 205

Leu Glu Asn Ala Tyr
    210
```

<210> SEQ ID NO 11
<211> LENGTH: 638
<212> TYPE: DNA
<213> ORGANISM: Mus musculus

<400> SEQUENCE: 11

```
atgcagccct cactagcccc gtgcctcatc tgcctacttg tgcacgctgc cttctgtgct    60
gtggagggcc aggggtggca agccttcagg aatgatgcca cagaggtcat cccagggctt   120
ggagagtacc ccgagcctcc tcctgagaac aaccagacca tgaaccgggc ggagaatgga   180
ggcagacctc cccaccatcc ctatgacgcc aaaggtgtgt ccgagtacag ctgccgcgag   240
ctgcactaca cccgcttcct gacagacggc ccatgccgca cgccaagcc ggtcaccgag   300 ttggtgtgct ccggccagtg cggccccgcg cggctgctgc ccaacgccat cgggcgcgtg   360
aagtggtggc gcccgaacgg accggatttc cgctgcatcc cggatcgcta ccgcgcgcag   420
cgggtgcagc tgctgtgccc cggggggcgcg gcgccgcgct cgcgcaaggt gcgtctggtg   480
gcctcgtgca agtgcaagcg cctcacccgc ttccacaacc agtcggagct caaggacttc   540
gggccggaga ccgcgcggcc gcagaagggt cgcaagccgc ggcccggcgc ccggggagcc   600
```

```
                                          aaagccaacc aggcggagct ggagaacgcc tactagag                       638
```

<210> SEQ ID NO 12
<211> LENGTH: 211
<212> TYPE: PRT
<213> ORGANISM: Mus musculus

<400> SEQUENCE: 12

```
Met Gln Pro Ser Leu Ala Pro Cys Leu Ile Cys Leu Leu Val His Ala
 1               5                  10                  15

Ala Phe Cys Ala Val Glu Gly Gln Gly Trp Gln Ala Phe Arg Asn Asp
            20                  25                  30

Ala Thr Glu Val Ile Pro Gly Leu Gly Glu Tyr Pro Glu Pro Pro
        35                  40                  45

Glu Asn Asn Gln Thr Met Asn Arg Ala Glu Asn Gly Gly Arg Pro Pro
    50                  55                  60

His His Pro Tyr Asp Ala Lys Asp Val Ser Glu Tyr Ser Cys Arg Glu
65                  70                  75                  80

Leu His Tyr Thr Arg Phe Leu Thr Asp Gly Pro Cys Arg Ser Ala Lys
                85                  90                  95

Pro Val Thr Glu Leu Val Cys Ser Gly Gln Cys Gly Pro Ala Arg Leu
            100                 105                 110

Leu Pro Asn Ala Ile Gly Arg Val Lys Trp Trp Arg Pro Asn Gly Pro
        115                 120                 125

Asp Phe Arg Cys Ile Pro Asp Arg Tyr Arg Ala Gln Arg Val Gln Leu
    130                 135                 140

Leu Cys Pro Gly Gly Ala Ala Pro Arg Ser Arg Lys Val Arg Leu Val
145                 150                 155                 160

Ala Ser Cys Lys Cys Lys Arg Leu Thr Arg Phe His Asn Gln Ser Glu
                165                 170                 175

Leu Lys Asp Phe Gly Pro Glu Thr Ala Arg Pro Gln Lys Gly Arg Lys
            180                 185                 190

Pro Arg Pro Gly Ala Arg Gly Ala Lys Ala Asn Gln Ala Glu Leu Glu
        195                 200                 205

Asn Ala Tyr
    210
```

<210> SEQ ID NO 13
<211> LENGTH: 674
<212> TYPE: DNA
<213> ORGANISM: Rattus norvegicus

<400> SEQUENCE: 13

```
gaggaccgag tgcccttcct ccttctggca ccatgcagct ctcactagcc ccttgccttg    60
cctgcctgct tgtacatgca gccttcgttg ctgtggagag ccaggggtgg caagccttca   120
agaatgatgc cacagaaatc atcccgggac tcagagagta cccagagcct cctcaggaac   180
tagagaacaa ccagaccatg aaccgggccg agaacggagg cagacccccc caccatcctt   240
atgacaccaa agacgtgtcc gagtacagct gccgcgagct gcactacacc cgcttcgtga   300
ccgacggccc gtgccgcagt gccaagccgg tcaccgagtt ggtgtgctcg ggccagtgcg   360
gccccgcgcg gctgctgccc aacgccatcg gcgcgtgaa gtggtggcgc ccgaacggac   420
ccgacttccg ctgcatcccg gatcgctacc gcgcgcagcg ggtgcagctg ctgtgccccg   480
gcggcgcggc gccgcgctcg cgcaaggtgc gtctggtggc ctcgtgcaag tgcaagcgcc   540
tcacccgctt ccacaaccag tcggagctca aggacttcgg acctgagacc gcgcggccgc   600
```

-continued

```
agaagggtcg caagccgcgg ccccgcgccc ggggagccaa agccaaccag gcggagctgg    660
agaacgccta ctag                                                      674
```

```
<210> SEQ ID NO 14
<211> LENGTH: 213
<212> TYPE: PRT
<213> ORGANISM: Rattus norvegicus

<400> SEQUENCE: 14
```

```
Met Gln Leu Ser Leu Ala Pro Cys Leu Ala Cys Leu Val His Ala
 1               5                  10                  15

Ala Phe Val Ala Val Glu Ser Gln Gly Trp Gln Ala Phe Lys Asn Asp
                20                  25                  30

Ala Thr Glu Ile Ile Pro Gly Leu Arg Glu Tyr Pro Glu Pro Gln
             35                  40                  45

Glu Leu Glu Asn Asn Gln Thr Met Asn Arg Ala Glu Asn Gly Gly Arg
 50                  55                  60

Pro Pro His His Pro Tyr Asp Thr Lys Asp Val Ser Glu Tyr Ser Cys
65                  70                  75                  80

Arg Glu Leu His Tyr Thr Arg Phe Val Thr Asp Gly Pro Cys Arg Ser
                85                  90                  95

Ala Lys Pro Val Thr Glu Leu Val Cys Ser Gly Gln Cys Gly Pro Ala
            100                 105                 110

Arg Leu Leu Pro Asn Ala Ile Gly Arg Val Lys Trp Trp Arg Pro Asn
        115                 120                 125

Gly Pro Asp Phe Arg Cys Ile Pro Asp Arg Tyr Arg Ala Gln Arg Val
    130                 135                 140

Gln Leu Leu Cys Pro Gly Gly Ala Ala Pro Arg Ser Arg Lys Val Arg
145                 150                 155                 160

Leu Val Ala Ser Cys Lys Cys Lys Arg Leu Thr Arg Phe His Asn Gln
                165                 170                 175

Ser Glu Leu Lys Asp Phe Gly Pro Glu Thr Ala Arg Pro Gln Lys Gly
            180                 185                 190

Arg Lys Pro Arg Pro Arg Ala Arg Gly Ala Lys Ala Asn Gln Ala Glu
        195                 200                 205

Leu Glu Asn Ala Tyr
    210
```

```
<210> SEQ ID NO 15
<211> LENGTH: 532
<212> TYPE: DNA
<213> ORGANISM: Bos torus

<400> SEQUENCE: 15
```

```
agaatgatgc cacagaaatc atccccgagc tgggcgagta ccccgagcct ctgccagagc    60
tgaacaacaa gaccatgaac cgggcggaga acggagggag acctccccac caccccttg    120 agaccaaaga cgcctccgag tacagctgcc gggagctgca ctcacccgc tacgtgaccg    180 atgggccgtg ccgcagcgcc aagccggtca ccgagctggt gtgctcgggc cagtgcggcc    240
cggcgcgcct gctgcccaac gccatcggcc gcggcaagtg gtggcgccca agcgggcccg    300
acttccgctg catccccgac cgctaccgcg cgcagcgggt gcagctgttg tgtcctggcg    360
gcgcggcgcc gcgcgcgcgc aaggtgcgc tggtggcctc gtgcaagtgc aagcgcctca    420
ctcgcttcca caaccagtcc gagctcaagg acttcgggcc cgaggccgcg cggccgcaaa    480
```
cgggccggaa gctgcggccc cgcgcccggg gcaccaaagc cagccgggcc ga    532

```
<210> SEQ ID NO 16
<211> LENGTH: 176
<212> TYPE: PRT
<213> ORGANISM: Bos torus

<400> SEQUENCE: 16
```

Asn Asp Ala Thr Glu Ile Ile Pro Glu Leu Gly Glu Tyr Pro Glu Pro
 1               5                  10                  15

Leu Pro Glu Leu Asn Asn Lys Thr Met Asn Arg Ala Glu Asn Gly Gly
            20                  25                  30

Arg Pro His His Pro Phe Glu Thr Lys Asp Ala Ser Glu Tyr Ser
        35                  40                  45

Cys Arg Glu Leu His Phe Thr Arg Tyr Val Thr Asp Gly Pro Cys Arg
 50                  55                  60

Ser Ala Lys Pro Val Thr Glu Leu Val Cys Ser Gly Gln Cys Gly Pro
 65                  70                  75                  80

Ala Arg Leu Leu Pro Asn Ala Ile Gly Arg Gly Lys Trp Trp Arg Pro
                85                  90                  95

Ser Gly Pro Asp Phe Arg Cys Ile Pro Asp Arg Tyr Arg Ala Gln Arg
            100                 105                 110

Val Gln Leu Leu Cys Pro Gly Gly Ala Ala Pro Arg Ala Arg Lys Val
        115                 120                 125

Arg Leu Val Ala Ser Cys Lys Cys Lys Arg Leu Thr Arg Phe His Asn
130                 135                 140

Gln Ser Glu Leu Lys Asp Phe Gly Pro Glu Ala Ala Arg Pro Gln Thr
145                 150                 155                 160

Gly Arg Lys Leu Arg Pro Arg Ala Arg Gly Thr Lys Ala Ser Arg Ala
                165                 170                 175

```
<210> SEQ ID NO 17
<211> LENGTH: 232
<212> TYPE: PRT
<213> ORGANISM: Homo sapiens

<400> SEQUENCE: 17
```

Met Glu Arg Cys Pro Ser Leu Gly Val Thr Leu Tyr Ala Leu Val Val
 1               5                  10                  15

Val Leu Gly Leu Arg Ala Thr Pro Ala Gly Gly Gln His Tyr Leu His
            20                  25                  30

Ile Arg Pro Ala Pro Ser Asp Asn Leu Pro Leu Val Asp Leu Ile Glu
        35                  40                  45

His Pro Asp Pro Ile Phe Asp Pro Lys Glu Lys Asp Leu Asn Glu Thr
 50                  55                  60

Leu Leu Arg Ser Leu Leu Gly Gly His Tyr Asp Pro Gly Phe Met Ala
 65                  70                  75                  80

Thr Ser Pro Pro Glu Asp Arg Pro Gly Gly Gly Gly Ala Ala Gly
                85                  90                  95

Gly Ala Glu Asp Leu Ala Glu Leu Asp Gln Leu Leu Arg Gln Arg Pro
            100                 105                 110

Ser Gly Ala Met Pro Ser Glu Ile Lys Gly Leu Glu Phe Ser Glu Gly
        115                 120                 125

Leu Ala Gln Gly Lys Lys Gln Arg Leu Ser Lys Leu Arg Arg Lys
130                 135                 140

Leu Gln Met Trp Leu Trp Ser Gln Thr Phe Cys Pro Val Leu Tyr Ala

```
                145                 150                 155                 160
Trp Asn Asp Leu Gly Ser Arg Phe Trp Pro Arg Tyr Val Lys Val Gly
                    165                 170                 175

Ser Cys Phe Ser Lys Arg Ser Cys Ser Val Pro Glu Gly Met Val Cys
                180                 185                 190

Lys Pro Ser Lys Ser Val His Leu Thr Val Leu Arg Trp Arg Cys Gln
                195                 200                 205

Arg Arg Gly Gly Gln Arg Cys Gly Trp Ile Pro Ile Gln Tyr Pro Ile
            210                 215                 220

Ile Ser Glu Cys Lys Cys Ser Cys
225                 230

<210> SEQ ID NO 18
<211> LENGTH: 420
<212> TYPE: DNA
<213> ORGANISM: Homo sapiens

<400> SEQUENCE: 18
gagctccggc gggtcagccg gactgtcggc ttcccggggc atctgggtcc ggcggggcac      60
agccctgggc gctgccgaag ccgccgccgc cgcctccgcg gcgagtacag gcggcttccc     120
ccggagcctg tgcagctcca gctcctcggg ggtggagaag tgggggggtgg gggtgatgta    180
tggggggaag aagggggagg ggccaacccc gagagagtca gtggtttcca tggtgatgga    240
gctgaaagtg caggaaattt aaaggcttgg accctgcgag acagacaaac cggtgccaac    300
gtgcgcggac gccgccgccg ccgccgccgc tggagtccgc cgggcagagc cggccgcgga    360
gcccggagca ggcggaggga agtgccccta gaaccagctc agccagcggc gcttgcacag    420

<210> SEQ ID NO 19
<211> LENGTH: 218
<212> TYPE: PRT
<213> ORGANISM: Homo sapiens

<400> SEQUENCE: 19

Met Pro Ser Leu Pro Ala Pro Ala Pro Leu Leu Leu Gly Leu
1               5                   10                  15

Leu Leu Gly Ser Arg Pro Ala Arg Gly Ala Gly Pro Glu Pro Pro
            20                  25                  30

Val Leu Pro Ile Arg Ser Glu Lys Glu Pro Leu Pro Val Arg Gly Ala
            35                  40                  45

Ala Gly Cys Thr Phe Gly Gly Lys Val Tyr Ala Leu Asp Glu Thr Trp
        50                  55                  60

His Pro Asp Leu Gly Glu Pro Phe Gly Val Met Arg Cys Val Leu Cys
65                  70                  75                  80

Ala Cys Glu Ala Pro Gln Trp Gly Arg Arg Thr Arg Gly Pro Gly Arg
                85                  90                  95

Val Ser Cys Lys Asn Ile Lys Pro Glu Cys Pro Thr Pro Ala Cys Gly
                100                 105                 110

Gln Pro Arg Gln Leu Pro Gly His Cys Cys Gln Thr Cys Pro Gln Glu
            115                 120                 125

Arg Ser Ser Ser Glu Arg Gln Pro Ser Gly Leu Ser Phe Glu Tyr Pro
        130                 135                 140

Arg Asp Pro Glu His Arg Ser Tyr Ser Asp Arg Gly Glu Pro Gly Ala
145                 150                 155                 160

Glu Glu Arg Ala Arg Gly Asp Gly His Thr Asp Phe Val Ala Leu Leu
                165                 170                 175
```

```
Thr Gly Pro Arg Ser Gln Ala Val Ala Arg Ala Arg Val Ser Leu Leu
            180                 185                 190

Arg Ser Ser Leu Arg Phe Ser Ile Ser Tyr Arg Arg Leu Asp Arg Pro
        195                 200                 205

Thr Arg Ile Arg Phe Ser Asp Ser Asn Gly
    210                 215

<210> SEQ ID NO 20
<211> LENGTH: 420
<212> TYPE: DNA
<213> ORGANISM: Homo sapiens

<400> SEQUENCE: 20
cccgggtcag cgcccgcccg cccgcgctcc tcccggccgc tcctcccgcc ccgcccggcc      60
cggcgccgac tctgcggccg cccgacgagc ccctcgcggc actgcccgg ccccggcccc     120 ggccccggcc ccctcccgcc gcaccgcccc cggcccggcc ctccgccctc cgcactcccg     180 cctcctccc tccgcccgct cccgcgccct cctccctccc tcctcccag ctgtcccgtt      240 cgcgtcatgc cgagcctccc ggcccgcgcg gccccgctgc tgctcctcgg gctgctgctg     300
ctcggctccc ggccggcccg cggcgccggc cccgagcccc ccgtgctgcc catccgttct     360
gagaaggagc cgctgcccgt tcggggagcg gcaggctgca ccttcggcgg gaaggtctat     420
```